United States Patent
Van Der Vliet et al.

(10) Patent No.: US 12,110,328 B2
(45) Date of Patent: Oct. 8, 2024

(54) SINGLE DOMAIN ANTIBODIES TARGETING CD1D

(71) Applicant: LAVA THERAPEUTICS N.V., Utrecht (NL)

(72) Inventors: Johannes Jelle Van Der Vliet, Utrecht (NL); Tanja Denise De Gruijl, Utrecht (NL); Hendrik Marinus Willem Verheul, Utrecht (NL); Renée Cornelia Gerarda De Bruin, Utrecht (NL); Roeland Lameris, Utrecht (NL)

(73) Assignee: LAVA THERAPEUTICS N.V., Utrecht (NL)

( * ) Notice: Subject to any disclaimer, the term of this patent is extended or adjusted under 35 U.S.C. 154(b) by 0 days.

(21) Appl. No.: 18/161,163

(22) Filed: Jan. 30, 2023

(65) Prior Publication Data

US 2024/0067726 A1 Feb. 29, 2024

Related U.S. Application Data

(63) Continuation of application No. 16/666,734, filed on Oct. 29, 2019, now Pat. No. 11,591,394, which is a continuation of application No. 15/546,406, filed as application No. PCT/NL2016/050064 on Jan. 27, 2016, now Pat. No. 10,501,541.

(30) Foreign Application Priority Data

Jan. 27, 2015 (NL) .................................... 2014192

(51) Int. Cl.
*C07K 16/28* (2006.01)
*C07K 16/30* (2006.01)

(52) U.S. Cl.
CPC ...... *C07K 16/2809* (2013.01); *C07K 16/2833* (2013.01); *C07K 16/30* (2013.01); *C07K 2317/565* (2013.01); *C07K 2317/569* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 5,723,309 A | 3/1998 | Bonneville | |
| 6,737,398 B1 | 5/2004 | Gelfand et al. | |
| 7,419,958 B2 | 9/2008 | Wilson et al. | |
| 7,582,300 B2 | 9/2009 | Gelfand et al. | |
| 7,728,114 B2 | 6/2010 | Mach et al. | |
| 8,012,484 B2 | 9/2011 | Linden et al. | |
| 8,084,020 B2 | 12/2011 | Exley et al. | |
| 8,153,426 B2 | 4/2012 | Moser et al. | |
| 8,178,098 B2 | 5/2012 | Lahn et al. | |
| 8,338,173 B2 | 12/2012 | Moser et al. | |
| 10,106,623 B2 | 10/2018 | Uhlin et al. | |
| 10,501,540 B2 | 12/2019 | Van et al. | |
| 10,501,541 B2 | 12/2019 | Van Der Vliet et al. | |
| 10,758,625 B2 | 9/2020 | Yu et al. | |
| 11,000,603 B2 | 5/2021 | Yu et al. | |
| 11,384,145 B2 | 7/2022 | Van Der Vliet et al. | |
| 11,591,394 B2 | 2/2023 | Van Der Vliet et al. | |
| 2015/0231234 A1* | 8/2015 | Exley ...................... A61P 37/08 424/265.1 |
| 2018/0142020 A1 | 5/2018 | Van Der Vliet et al. | |
| 2019/0263908 A1 | 8/2019 | Van Der Vliet et al. | |
| 2020/0115450 A1 | 4/2020 | Van Der Vliet et al. | |
| 2021/0284730 A1 | 9/2021 | Ganesan et al. | |
| 2022/0098301 A1 | 3/2022 | Van Der Vliet et al. | |
| 2023/0212290 A1 | 7/2023 | Vliet | |

FOREIGN PATENT DOCUMENTS

| | | |
|---|---|---|
| CN | 104144700 A | 11/2014 |
| EP | 1229790 A1 | 8/2002 |
| EP | 1778836 B1 | 8/2010 |
| EP | 1372668 B1 | 12/2011 |
| EP | 1812015 B1 | 1/2012 |
| EP | 3105252 B1 | 7/2019 |
| EP | 3144388 B1 | 7/2020 |
| EP | 4118121 A1 | 1/2023 |
| WO | WO-9500163 A1 | 1/1995 |
| WO | WO-0122816 A1 | 4/2001 |
| WO | WO-0182960 A1 | 11/2001 |
| WO | WO-0198357 A2 | 12/2001 |
| WO | WO-02076401 A2 | 10/2002 |
| WO | WO-02080967 A1 | 10/2002 |
| WO | WO-03068821 A2 | 8/2003 |

(Continued)

OTHER PUBLICATIONS

Allison et al., "Structure of a human γδ T-cell antigen receptor", Nature. Jun. 14, 2001, vol. 411, 820-824.

Beckman Coulter, Inc., "TCR Vgamma 9", https://www.beckmancoulter.com/wsrportal/page/itemDetails?itemNumber=IM1463#2/10//0/25/1/0/asc/2/IM14631//0/1//0/, retrieved on Sep. 26, 2014, 1 page.

Bedouelle et al., "Diversity and junction residues as hotspots of binding energy in an antibody neutralizing the dengue virus", FEBS J. (2006); 273(1):34-46.

Brown, M. et al. "Tolerance to Single, but not Multiple, Amino Acid Replacements in Antibody VH CDR2," The Journal of Immunology, 1996, 156: 3285-3291.

Broxmeyer, et al., "CD1d expression on and regulation of murine hematopoietic stem and progenitor cells", Blood. Jun. 14, 2012; 119(24): 5731-5741. Prepublished online Apr. 25, 2012.

(Continued)

*Primary Examiner* — Laura B Goddard
(74) *Attorney, Agent, or Firm* — COOLEY LLP

(57) ABSTRACT

The invention relates to compounds, in particular polypeptides that specifically bind to the non-classical MHC protein CD1d and modulate CD1d-mediated biological functions. The invention in particular relates to such compounds and polypeptides comprising or consisting of at least one single domain antibody, and wherein at least one single domain antibody specifically binds to CD1d. Also provided is for methods and use employing such compounds, polypeptides and/or single-domain antibodies.

15 Claims, 11 Drawing Sheets

Figure 1:
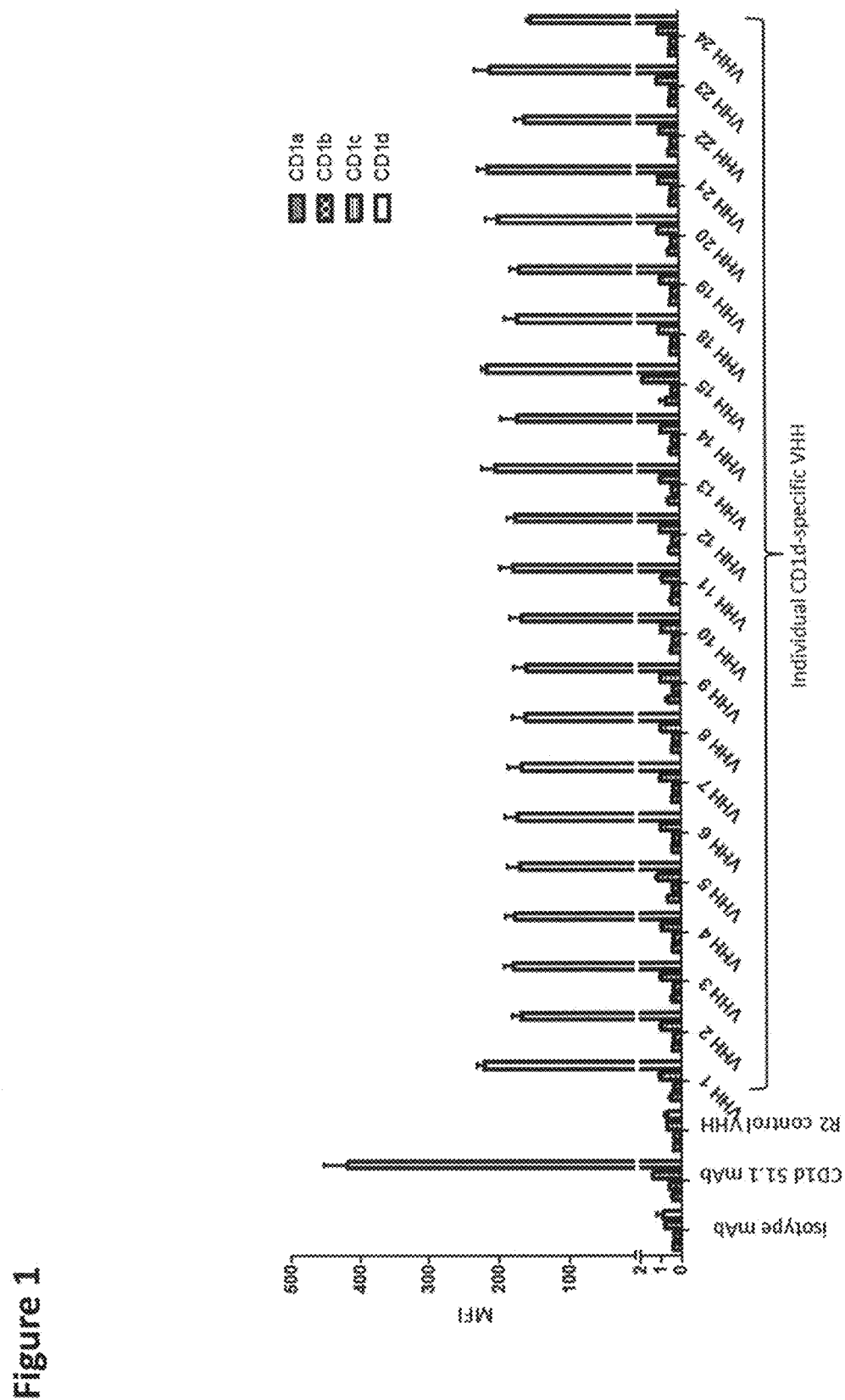

Specification includes a Sequence Listing.

(56) References Cited

FOREIGN PATENT DOCUMENTS

| WO | WO-03080672 A1 | 10/2003 |
|---|---|---|
| WO | WO-03092615 A2 | 11/2003 |
| WO | WO-2004062551 A2 | 7/2004 |
| WO | WO-2005046711 A2 | 5/2005 |
| WO | WO-2006017954 A1 | 2/2006 |
| WO | WO-2006060117 A2 | 6/2006 |
| WO | WO-2008006895 A2 | 1/2008 |
| WO | WO-2010130830 A2 | 11/2010 |
| WO | WO-2013053021 A1 | 4/2013 |
| WO | WO-2013110531 A1 | 8/2013 |
| WO | WO-2013147606 A1 | 10/2013 |
| WO | WO-2013174403 A1 | 11/2013 |
| WO | WO-2013174404 A1 | 11/2013 |
| WO | WO-2013174509 A1 | 11/2013 |
| WO | WO-2013174510 A1 | 11/2013 |
| WO | WO-2014127785 A1 | 8/2014 |
| WO | WO-2014127906 A1 | 8/2014 |
| WO | WO-2014210522 A1 | 12/2014 |
| WO | WO-2015121383 A1 | 8/2015 |
| WO | WO-2015156673 A1 | 10/2015 |
| WO | WO-2015174439 A1 | 11/2015 |
| WO | WO-2016001276 A1 | 1/2016 |
| WO | WO-2016081518 A2 | 5/2016 |
| WO | WO-2016122320 A1 | 8/2016 |
| WO | WO-2016165302 A1 | 10/2016 |
| WO | WO-2017086367 A1 | 5/2017 |
| WO | WO-2017185662 A1 | 11/2017 |
| WO | WO-2018023111 A1 | 2/2018 |
| WO | WO-2018140831 A2 | 8/2018 |
| WO | WO-2018229163 A1 | 12/2018 |
| WO | WO-2019070424 A1 | 4/2019 |
| WO | WO-2019195535 A1 | 10/2019 |
| WO | WO-2020010250 A2 | 1/2020 |
| WO | WO-2020172596 A1 | 8/2020 |
| WO | WO-2020227457 A1 | 11/2020 |
| WO | WO-2021032960 A1 | 2/2021 |
| WO | WO-2021032961 A1 | 2/2021 |
| WO | WO-2021032963 A1 | 2/2021 |
| WO | WO-2021173896 A1 | 9/2021 |
| WO | WO-2021183845 A1 | 9/2021 |
| WO | WO-2022093888 A1 | 5/2022 |

OTHER PUBLICATIONS

Colman, P. M., "Effects of amino acid sequence changes on antibody-antigen interactions", Res Immunol. Jan. 1994; 145(1): 33-6.

Communication Pursuant to Article 94(3) EPC for European Application No. 15 722 781.0, dated Feb. 7, 2018, 5 pages.

Dondelinger et al., "Understanding the Significance and Implications of Antibody Numbering and Antigen-Binding Surface/Residue Definition," Frontiers in Immunology, Oct. 2018, 9: 2278, 15 pages.

Edwards, B.M. et al., "The Remarkable Flexibility of the Human Antibody Repertoire; Isolation of Over One Thousand Different Antibodies to a Single Protein, BLyS," Journal of Molecular Biology, Nov. 14, 2003, 334(1), pp. 103-118.

Ferrini et al., "Monoclonal antibodies which react with the T cell receptor γ/σ recognize different subsets of CD3+WT31-T lymphocytes", Eur. J. Immunol. 1989. 19:57-61.

Ferrini et al., " Re-targeting of human lymphocytes expressing the T-cell receptor gamma/delta to ovarian carcinoma cells by the use of bispecific monoclonal antibodies", Int. J. Cancer: 44, 245-250 (1989).

Harlow et al., "Antibody Response", Chapter 4, and "Immunizations", Chapter 5, Antibodies, A Laboratory Manual, Cold Spring Harbor laboratory, 1988, pp. 37-47, 55-59.

International Search Report and Written Opinion for International Application No. PCT/NL2016/050064, mailed May 27, 2016, 12 pages.

International Search Report issued to International Application No. PCT/NL2015/050235, mailed Jul. 10, 2015, 6 pages.

Lameris, et al., "Exploiting the CD1d-iNKT cell axis for potentiation of DC-based cancer vaccines", Methods Mol Biol., 2014; 1139:155-65.

Lameris et al. "Generation and characterization of CD1d-specific single-domain antibodies with distinct functional features", Immunology, (2016); 149(1):111-121.

Langerak, AW, et al., "Immunophenotypic and immunogenotypic characteristics of TCRγδ+ T cell acute lymphoblastic leukemia", Leukemia (1999); 13, 206-214.

Lloyd, C., et al., "Modelling the human immune response: performance of a 1011 human antibody repertoire against a broad panel of therapeutically relevant antigens", Protein Engineering, Design and Selection, Mar. 2009, 22(3), pp. 159-168.

Ma et al.,"CD1d blockade suppresses the capacity of immature dendritic cells to prime allogeneic T cell response", Journal of Surgical Research, pp. 894-899, vol. 1. 183, No. 2 (Feb. 2013).

Miossec et al., "Further analysis of the T cell receptor gamma/delta+ peripheral lymphocyte subset. The V delta 1 gene segment is expressed with either C alpha or C delta", J. Exp. Med., vol. 171, Apr. 1990, 1171-1188.

Monzon-Casanov et al., "CD1d Expression in Paneth Cells and Rat Exocrine Pancreas Revealed by Novel Monoclonal Antibodies Which Differentially Affect NKT Cell Activation", PLOS One, pp. e1308, vol. 5, No. 9, (Sep. 2010), 15 pages.

Muyldermans, S. (2013) "Nanobodies: Natural Single-Domain Antibodies". Annu Rev Biochem, 82:775-797.

Muyldermans, S., "Single domain camel antibodies: current status," Rev. Mol. Biotechnol. 74:277-302, 2001.

Oberg et al., "Novel Bispecific Antibodies Increase γδ T-Cell Cytotoxicity against Pancreatic Cancer Cells", Cancer Res; 74(5); 1349-60, 2014.

Roovers et al., "Efficient inhibition of EGFR signaling and of tumour growth by antagonistic anti-EFGR Nanobodies," Cancer Immunol Immunother, Mar. 2007; 56(3): 303-17.

Rossjohn et al., "Recognition of CD1d-restricted antigens by natural killer T cells", Nat Rev Immunol., Dec. 2012;12(12):845-57.

Rudikoff, S. et al. "Single amino acid substitution altering antigen-binding specificity", Proc Natl Acad Sci, (Mar. 1982); 79:1979-1983.

Saerens et al., "Identification of a Universal VHH Framework to Graft Non-canonical Antigen-binding Loops of Camel Single-domain Antibodies", J. Mol. Biol. (2005) 352, 597-607.

Siontorou et al., "Nanobodies as novel agents for disease diagnosis and therapy", International Journal of Nanomedicine, p. 4215 (Nov. 2013).

Smolarek et al., Variable fragments of heavy chain antibodies (VHHs): a new magic bullet molecule of medicine?, Postepy Hig Med Dosw (online), 2012; 66: 348-358.

Spanoudakis et al., "Regulation of multiple myeloma survival and progression by CD1d", Blood Mar. 12, 2009; 113(11): 2498-2507. Epub Dec. 3, 2008.

Szereday, L. et al., "γ/δ T cell subsets in patients with active *Mycobacterium tuberculosis* infection and tuberculin anergy", Clin Exp Immunol, Feb. 2003; 131(2): 287-291.

Tamura, M. et al., "Structural correlates of an anticarcinoma antibody: identification of specificity-determining residues (SDRs) and development of a minimally immunogenic antibody variant by retention of SDRs only," J. Immunol., 2000, vol. 164, No. 3, pp. 1432-1441.

Teng et al., "CD1d Activation and Blockade: A New Antitumor Strategy", J Immunol., 182(6):3366-3371 (2009).

Vajdos et al., "Comprehensive Functional Maps of the Antigen-binding Site of an Anti-ErbB2 Antibody Obtained with Shotgun Scanning Mutagenesis," J Mol Biol, Jul. 5, 2002; 320(2): 415-28.

Vecchi et al., "Increased Jejunal Intraepithelial Lymphocytes Bearing γ/σ T-Cell Receptor in Dermatitis Herpetiformis", Gastroenterology, 1992; 102: 1499-1505.

Viale et al., "TCR gamma/delta positive lymphocytes after allogeneic bone marrow transplantation", Bone Marrow Transplantation 1992, 10:249-253.

Vincke, C. et al., "General strategy to humanize a camelid single-domain antibody and identification of a universal humanized nanobody scaffold", J Biol Chem. (2009); 284(5):3273-3284.

(56) References Cited

OTHER PUBLICATIONS

Vincke et al., "Introduction to Heavy Chain Antibodies and Derived Nanobodies", Methods in Molecular Biology, pp. 15-26, vol. 911 (Jul. 2012).

White et al., "Antibodies to C0D1d enhance thymic expression of invariant NKT TCR and increase the presence of NOD thymic invariant NKT cells", Developmental and Comparative Immunology, pp. 943-956, vol. 32, No. 8, (Jan. 2008).

Winkler, K., et al., "Changing the antigen binding specificity by single point mutations of an anti-p24 (HIV-1) antibody", The Journal of Immunology (Oct. 15, 2000); 165(8): 4505-4514.

Written Opinion of the International Searching Authority for International Application No. PCT/NL2015/050235, mailed Jul. 10, 2015, 8 pages.

Wrobel, P., et al., Lysis of a Broad Range of Epithelial Tumour Cells by Human gamma delta T Cells: Involvement of NKG2D ligands and T-cell Receptor-versus NKG2D-dependent Recognition, Scandinavian Journal of Immunology, 2007, 66, 320-328.

Yu et al., "The diverse functions of CD1d-restricted NKT cells and their potential for immunotherapy", pp. 42-55, vol. 100, No. 1 (Aug. 2005).

Yue et al., "CD1d ligation on human monocytes directly signals rapid NF-B activation and production of bioactive IL-12", Proceedings of the National Academy of Sciences, pp. 11811-11816, vol. 102, No. 1 (Aug. 2005).

Yue et al., "Direct CD1d-Mediated Stimulation of APC IL-12 Production and Protective Immune Response to Virus Infection In Vivo", J Immunol., 184(1): 268-276 (2010).

Zabetakis et al., "Contributions of the Complementarity Determining Regions to the Thermal Stability of a Single-Domain Antibody", PLOS One, Oct. 2013, vol. 8, Issue 10, e77678, 1-7.

Zhou et al., "Anti-γδ TCR antibody-expanded γδ T cells: a better choice for the adoptive immunotherapy of lymphoid malignancies", Cellular & Molecular Immunology (2012) 9, 34-44.

* cited by examiner

SEQUENCE LISTING

```
Sequence total quantity: 84
SEQ ID NO: 1           moltype = AA  length = 126
FEATURE                Location/Qualifiers
source                 1..126
                       mol_type = protein
                       organism = synthetic construct
SEQUENCE: 1
VQLVESGGGL VQAGGSLRLS CAASGSSFSS YTMGWFRQAP GKEREIVAAI RWSGESPYYA   60
DSVKGRFTIS RDNAKNTLYL QMNSLKPEDT AVYFCAARLV PPGIPIERSL ENMNYWGKGT  120
LVTVSS                                                             126

SEQ ID NO: 2           moltype = AA  length = 126
FEATURE                Location/Qualifiers
source                 1..126
                       mol_type = protein
                       organism = synthetic construct
SEQUENCE: 2
VQLVESGGGS VQAGGSLRLS CAASGRSFSS YTMGWCRQAP GKERECVAVI RWSGESPYYA   60
DSVKGRFTIS RDNAKNTVYL QMNSLKPEDT AVYYCAARLV PPGIPIERTL ESMNYWGKGT  120
LVTVSS                                                             126

SEQ ID NO: 3           moltype = AA  length = 127
FEATURE                Location/Qualifiers
source                 1..127
                       mol_type = protein
                       organism = synthetic construct
SEQUENCE: 3
QVQLVESGGG LVQAGGSLRL SCAASGSSFS SYTMGWFRQA PGKEREIVAA IRWSGESPIY   60
ADSVKGRFTI SRDNAKNTLY LQMNSLKPED TAVYYCAARL VPPGIPIERT LESMRYWGKG  120
TLVTVSS                                                            127

SEQ ID NO: 4           moltype = AA  length = 130
FEATURE                Location/Qualifiers
source                 1..130
                       mol_type = protein
                       organism = synthetic construct
SEQUENCE: 4
EVQLVESGGG LVQAGGSLGL SCAASGRSFS SYTMGVIRWS GESPYYADSV KGAIRWSGES   60
PYYADSVKGR FTISRDNAKN TLYLQMNNLK PEDTAVYYCA ARLVPPGIPI ERTLESMKDW  120
GKGTLVTVSS                                                         130

SEQ ID NO: 5           moltype = AA  length = 129
FEATURE                Location/Qualifiers
source                 1..129
                       mol_type = protein
                       organism = synthetic construct
SEQUENCE: 5
VQLVESGGGL VQAGGSLRLS CAASGSSFSS YTMGAIRWSD ESPIYAGSVK GGIRWSDESP   60
IYADSVKGRF TISRDNAKNT LYLQMNSLKP EDTAVYYCAA RLVPPGIPIP RTSESMRYWG  120
KGTLVTVSS                                                          129
```

```
SEQ ID NO: 6              moltype = AA  length = 130
FEATURE                   Location/Qualifiers
source                    1..130
                          mol_type = protein
                          organism = synthetic construct
SEQUENCE: 6
QVQLVESGGG LVQAGDSLRL SCAASGSSFS SYTMAAIRWS DESPYYSDSV KGAIRWSGES    60
PIYADSVKGR FTISRDNAKN TLYLQMNSLK PEDTAVYNCA ARLVPPGIPI ERTLESMRYW   120
GKGTLVTVSS                                                          130

SEQ ID NO: 7              moltype = AA  length = 129
FEATURE                   Location/Qualifiers
source                    1..129
                          mol_type = protein
                          organism = synthetic construct
SEQUENCE: 7
EVQLVESGGG LVQAGGSLRL SCAASVSSFS SYTMGTIRTG GSTNYADSVK GGIRWDDENP    60
YYADSVKGRF TISRDNAKNT LYLQMNSLKP EDTANYYCAA RLVPPGIPFE RTLENMRYWG   120
KGTLVTVSS                                                           129

SEQ ID NO: 8              moltype = AA  length = 130
FEATURE                   Location/Qualifiers
source                    1..130
                          mol_type = protein
                          organism = synthetic construct
SEQUENCE: 8
EVQLVESGGG LVQAGGSLRL SCAASGSSFS SYTMGAIRWS GESPYYADSV KGAIRWDGES    60
PIYAESVKGR FTISRDNAKN TLYLQMNSLK PEDTAVYYCA ARLVPPGIPI ERTLESMRYW   120
GKGTLVTVSS                                                          130

SEQ ID NO: 9              moltype = AA  length = 130
FEATURE                   Location/Qualifiers
source                    1..130
                          mol_type = protein
                          organism = synthetic construct
SEQUENCE: 9
EVQLVESGGG SVQAGGSLRL SCAASGRSFS SYTMGAIRWS GESPYYADSV KGVIRWSGES    60
PYYADSVKGR FTISRDNAKN TVYLQMASLK PDDTAVYYCA ARLVPPGIPI ERTLESMNYW   120
GKGTLVTVSS                                                          130

SEQ ID NO: 10             moltype = AA  length = 130
FEATURE                   Location/Qualifiers
source                    1..130
                          mol_type = protein
                          organism = synthetic construct
SEQUENCE: 10
QVQLVESGGG LVQAGGSLRL SCAASGSSFS SYTMGAIRWS GESPYYADSV KGAIRWSDES    60
PIYAGSVKGR FTISRDNAKN TLYLQMNSLK PEDTAVYYCA ARLVPPGIPI ERTLESMRYW   120
GKGTLVTVSS                                                          130

SEQ ID NO: 11             moltype = AA  length = 129
FEATURE                   Location/Qualifiers
source                    1..129
                          mol_type = protein
                          organism = synthetic construct
SEQUENCE: 11
EVQLVESGGG LVQAGGSLRL SCAASGSSFS SYTMGSINNG GSTKYADSVK GAIRWSDESP    60
YYSDSVKGRF TISRDNAKNT LYLQMNSLKP EDTAVYYCSA RLVPPGIPIE RTLENMRYSG   120
KGTLVTVSS                                                           129

SEQ ID NO: 12             moltype = AA  length = 122
FEATURE                   Location/Qualifiers
source                    1..122
                          mol_type = protein
                          organism = synthetic construct
SEQUENCE: 12
QVQLVESGGG LVQAGGSLRL SCAASGSMFS DNVMGAIRWS GESPYYVDSV KGTIRTGGST    60
NYADSVKGRF TISRDNAKNT VYLQMNSLKP EDTAVYYCRH TIPVPSTPYD YWGQGTQVTV   120
SS                                                                  122

SEQ ID NO: 13             moltype = AA  length = 130
FEATURE                   Location/Qualifiers
source                    1..130
                          mol_type = protein
                          organism = synthetic construct
SEQUENCE: 13
QVQLVESGGG LVQAGGSLGL SCAASGRSFS SYTMGAIRWS GESPIYADSV KGAIRWSGES    60
PYYADSVKGR FTISRDNAKN TLYLQMNSLK PEDTAVYYCA ARLVPPGIPI ERTLENMNYW   120
```

```
GKGTLVTVSS                                                                    130

SEQ ID NO: 14           moltype = AA  length = 129
FEATURE                 Location/Qualifiers
source                  1..129
                        mol_type = protein
                        organism = synthetic construct
SEQUENCE: 14
VQLVESGGGL VQAGGSLRLS CAASGSSFSS YTMGGIRWSG ESPYYADSVK GAIRWSGESP              60
YYADSVKGRF TISRDNAKNT LYLQMNSLKP EDTAVYYCAA RLVPPGIPIE RTLESMNYWG              120
KGTLVTVSS                                                                     129

SEQ ID NO: 15           moltype = AA  length = 130
FEATURE                 Location/Qualifiers
source                  1..130
                        mol_type = protein
                        organism = synthetic construct
SEQUENCE: 15
QVQLVESGGG LVQAGGSLRL SCAASGSSFS SYTMGAIRWS GESPYYADSV KGAIRWSGES              60
PIYADSVKGR FTISRDNAKN TLYLQMNSLK PEDTAVYYCA ARLVPPGIPI ERTLESMKDW              120
GKGTLVTVSS                                                                    130

SEQ ID NO: 16           moltype = AA  length = 129
FEATURE                 Location/Qualifiers
source                  1..129
                        mol_type = protein
                        organism = synthetic construct
SEQUENCE: 16
QVQLVESGGG LVQAGGSLRL SCAASGSSFS SYTMTVISSS GSTNYADSVK GGIRWSGESP              60
YYADSVKGRF TISRDNAKNT LYLQMNSLKP EDTAVYYCAA RLVPPGIPIE RTLESMRYWG              120
KGTLVTVSS                                                                     129

SEQ ID NO: 17           moltype = AA  length = 129
FEATURE                 Location/Qualifiers
source                  1..129
                        mol_type = protein
                        organism = synthetic construct
SEQUENCE: 17
VQLVESGGGL VQAGGSLRLS CAASGSSFSS YTMGVIRWSG ESPYYADSVK GAIRWSGESP              60
YYGDSVKGRF TISRDNAKNT LYLQMNSLKP EDTAVYYCAA RLVPPGIPIG RTLESMNNWG              120
KGTLVTVSS                                                                     129

SEQ ID NO: 18           moltype = AA  length = 130
FEATURE                 Location/Qualifiers
source                  1..130
                        mol_type = protein
                        organism = synthetic construct
SEQUENCE: 18
QVQLVESGGG LVQAGGSLRL SCAASGSSFS SYTMGAIRWS DESPIYAGSV KGAIRWSGES              60
PYYADSVKGR FTISRDNAKN TLYLQMHSLK PEDTAVYYCA ARLVPPGIPI ERALENMNYW              120
GKGTLVTVSS                                                                    130

SEQ ID NO: 19           moltype = AA  length = 130
FEATURE                 Location/Qualifiers
source                  1..130
                        mol_type = protein
                        organism = synthetic construct
SEQUENCE: 19
EVQLVESGGG LVQAGGSLRL SCAASGSSFS SYTMGAIRWS DESPYYSDSV KGAIRWSDES              60
PIYADSVKGR FTISRDNAKN TLYLQMHSLK PEDTAFYYCA ARLVPPGIPI ERTLESMRYW              120
GKGTLVTVSS                                                                    130

SEQ ID NO: 20           moltype = AA  length = 129
FEATURE                 Location/Qualifiers
source                  1..129
                        mol_type = protein
                        organism = synthetic construct
SEQUENCE: 20
EVQLVESGGG LVQAGGSLRL SCAASGRSFS SYTMGTIRTG GSTNYADSVK GAIRWSGESP              60
YYADSVKGRF TISRDNAKNT NYLQMNSLKP ELTAVYYCAA RLVPPGIPIE RSLENMNYWG              120
KGTLVTVSS                                                                     129

SEQ ID NO: 21           moltype = AA  length = 121
FEATURE                 Location/Qualifiers
source                  1..121
                        mol_type = protein
                        organism = synthetic construct
SEQUENCE: 21
QVQLVESGGG LVQAGGSLRL SCAASGSIFS INAMGAIRWS GESPYYADSV KGVISSSGST              60
```

```
NYADSVKGRF TISRDNAKNT AYLQMNSLKV EDTAVYYCAA HVAGFDEYNY WGQGTQVTVS   120
S                                                                  121

SEQ ID NO: 22          moltype = AA  length = 10
FEATURE                Location/Qualifiers
source                 1..10
                       mol_type = protein
                       organism = synthetic construct
SEQUENCE: 22
GSSFSSYTMG                                                          10

SEQ ID NO: 23          moltype = AA  length = 10
FEATURE                Location/Qualifiers
source                 1..10
                       mol_type = protein
                       organism = synthetic construct
SEQUENCE: 23
GRSFSSYTMG                                                          10

SEQ ID NO: 24          moltype = AA  length = 10
FEATURE                Location/Qualifiers
source                 1..10
                       mol_type = protein
                       organism = synthetic construct
SEQUENCE: 24
GSSFSSYTMG                                                          10

SEQ ID NO: 25          moltype = AA  length = 10
FEATURE                Location/Qualifiers
source                 1..10
                       mol_type = protein
                       organism = synthetic construct
SEQUENCE: 25
GRSFSSYTMG                                                          10

SEQ ID NO: 26          moltype = AA  length = 10
FEATURE                Location/Qualifiers
source                 1..10
                       mol_type = protein
                       organism = synthetic construct
SEQUENCE: 26
GSSFSSYTMG                                                          10

SEQ ID NO: 27          moltype = AA  length = 10
FEATURE                Location/Qualifiers
source                 1..10
                       mol_type = protein
                       organism = synthetic construct
SEQUENCE: 27
GSSFSSYTMA                                                          10

SEQ ID NO: 28          moltype = AA  length = 10
FEATURE                Location/Qualifiers
source                 1..10
                       mol_type = protein
                       organism = synthetic construct
SEQUENCE: 28
VSSFSSYTMG                                                          10

SEQ ID NO: 29          moltype = AA  length = 10
FEATURE                Location/Qualifiers
source                 1..10
                       mol_type = protein
                       organism = synthetic construct
SEQUENCE: 29
GSSFSSYTMG                                                          10

SEQ ID NO: 30          moltype = AA  length = 10
FEATURE                Location/Qualifiers
source                 1..10
                       mol_type = protein
                       organism = synthetic construct
SEQUENCE: 30
GRSFSSYTMG                                                          10

SEQ ID NO: 31          moltype = AA  length = 10
FEATURE                Location/Qualifiers
source                 1..10
                       mol_type = protein
```

```
SEQUENCE: 31
GSSFSSYTMG                                                                      10

SEQ ID NO: 32           moltype = AA   length = 10
FEATURE                 Location/Qualifiers
source                  1..10
                        mol_type = protein
                        organism = synthetic construct
SEQUENCE: 32
GSSFSSYTMG                                                                      10

SEQ ID NO: 33           moltype = AA   length = 10
FEATURE                 Location/Qualifiers
source                  1..10
                        mol_type = protein
                        organism = synthetic construct
SEQUENCE: 33
GSMFSDNVMG                                                                      10

SEQ ID NO: 34           moltype = AA   length = 10
FEATURE                 Location/Qualifiers
source                  1..10
                        mol_type = protein
                        organism = synthetic construct
SEQUENCE: 34
GRSFSSYTMG                                                                      10

SEQ ID NO: 35           moltype = AA   length = 10
FEATURE                 Location/Qualifiers
source                  1..10
                        mol_type = protein
                        organism = synthetic construct
SEQUENCE: 35
GSSFSSYTMG                                                                      10

SEQ ID NO: 36           moltype = AA   length = 10
FEATURE                 Location/Qualifiers
source                  1..10
                        mol_type = protein
                        organism = synthetic construct
SEQUENCE: 36
GSSFSSYTMG                                                                      10

SEQ ID NO: 37           moltype = AA   length = 10
FEATURE                 Location/Qualifiers
source                  1..10
                        mol_type = protein
                        organism = synthetic construct
SEQUENCE: 37
GSSFSSYTMT                                                                      10

SEQ ID NO: 38           moltype = AA   length = 10
FEATURE                 Location/Qualifiers
source                  1..10
                        mol_type = protein
                        organism = synthetic construct
SEQUENCE: 38
GSSFSSYTMG                                                                      10

SEQ ID NO: 39           moltype = AA   length = 10
FEATURE                 Location/Qualifiers
source                  1..10
                        mol_type = protein
                        organism = synthetic construct
SEQUENCE: 39
GSSFSSYTMG                                                                      10

SEQ ID NO: 40           moltype = AA   length = 10
FEATURE                 Location/Qualifiers
source                  1..10
                        mol_type = protein
                        organism = synthetic construct
SEQUENCE: 40
GSSFSSYTMG                                                                      10

SEQ ID NO: 41           moltype = AA   length = 10
FEATURE                 Location/Qualifiers
source                  1..10
```

```
                            mol_type = protein
                            organism = synthetic construct
SEQUENCE: 41
GRSFSSYTMG                                                              10

SEQ ID NO: 42               moltype = AA  length = 10
FEATURE                     Location/Qualifiers
source                      1..10
                            mol_type = protein
                            organism = synthetic construct
SEQUENCE: 42
GSIFSINAMG                                                              10

SEQ ID NO: 43               moltype = AA  length = 17
FEATURE                     Location/Qualifiers
source                      1..17
                            mol_type = protein
                            organism = synthetic construct
SEQUENCE: 43
AIRWSGESPY YADSVKG                                                      17

SEQ ID NO: 44               moltype = AA  length = 17
FEATURE                     Location/Qualifiers
source                      1..17
                            mol_type = protein
                            organism = synthetic construct
SEQUENCE: 44
VIRWSGESPY YADSVKG                                                      17

SEQ ID NO: 45               moltype = AA  length = 17
FEATURE                     Location/Qualifiers
source                      1..17
                            mol_type = protein
                            organism = synthetic construct
SEQUENCE: 45
AIRWSGESPI YADSVKG                                                      17

SEQ ID NO: 46               moltype = AA  length = 17
FEATURE                     Location/Qualifiers
source                      1..17
                            mol_type = protein
                            organism = synthetic construct
SEQUENCE: 46
AIRWSGESPY YADSVKG                                                      17

SEQ ID NO: 47               moltype = AA  length = 17
FEATURE                     Location/Qualifiers
source                      1..17
                            mol_type = protein
                            organism = synthetic construct
SEQUENCE: 47
GIRWSDESPI YADSVKG                                                      17

SEQ ID NO: 48               moltype = AA  length = 17
FEATURE                     Location/Qualifiers
source                      1..17
                            mol_type = protein
                            organism = synthetic construct
SEQUENCE: 48
AIRWSGESPI YADSVKG                                                      17

SEQ ID NO: 49               moltype = AA  length = 17
FEATURE                     Location/Qualifiers
source                      1..17
                            mol_type = protein
                            organism = synthetic construct
SEQUENCE: 49
GIRWDDENPY YADSVKG                                                      17

SEQ ID NO: 50               moltype = AA  length = 17
FEATURE                     Location/Qualifiers
source                      1..17
                            mol_type = protein
                            organism = synthetic construct
SEQUENCE: 50
AIRWDGESPI YAESVKG                                                      17

SEQ ID NO: 51               moltype = AA  length = 17
FEATURE                     Location/Qualifiers
```

```
                          -continued source                    1..17
                          mol_type = protein
                          organism = synthetic construct
SEQUENCE: 51
VIRWSGESPY YADSVKG                                                    17

SEQ ID NO: 52             moltype = AA  length = 17
FEATURE                   Location/Qualifiers
source                    1..17
                          mol_type = protein
                          organism = synthetic construct
SEQUENCE: 52
AIRWSDESPI YAGSVKG                                                    17

SEQ ID NO: 53             moltype = AA  length = 17
FEATURE                   Location/Qualifiers
source                    1..17
                          mol_type = protein
                          organism = synthetic construct
SEQUENCE: 53
AIRWSDESPY YSDSVKG                                                    17

SEQ ID NO: 54             moltype = AA  length = 16
FEATURE                   Location/Qualifiers
source                    1..16
                          mol_type = protein
                          organism = synthetic construct
SEQUENCE: 54
TIRTGGSTNY ADSVKG                                                     16

SEQ ID NO: 55             moltype = AA  length = 17
FEATURE                   Location/Qualifiers
source                    1..17
                          mol_type = protein
                          organism = synthetic construct
SEQUENCE: 55
AIRWSGESPY YADSVKG                                                    17

SEQ ID NO: 56             moltype = AA  length = 17
FEATURE                   Location/Qualifiers
source                    1..17
                          mol_type = protein
                          organism = synthetic construct
SEQUENCE: 56
AIRWSGESPY YADSVKG                                                    17

SEQ ID NO: 57             moltype = AA  length = 17
FEATURE                   Location/Qualifiers
source                    1..17
                          mol_type = protein
                          organism = synthetic construct
SEQUENCE: 57
AIRWSGESPI YADSVKG                                                    17

SEQ ID NO: 58             moltype = AA  length = 17
FEATURE                   Location/Qualifiers
source                    1..17
                          mol_type = protein
                          organism = synthetic construct
SEQUENCE: 58
GIRWSGESPY YADSVKG                                                    17

SEQ ID NO: 59             moltype = AA  length = 17
FEATURE                   Location/Qualifiers
source                    1..17
                          mol_type = protein
                          organism = synthetic construct
SEQUENCE: 59
AIRWSGESPY YGDSVKG                                                    17

SEQ ID NO: 60             moltype = AA  length = 17
FEATURE                   Location/Qualifiers
source                    1..17
                          mol_type = protein
                          organism = synthetic construct
SEQUENCE: 60
AIRWSGESPY YADSVKG                                                    17

SEQ ID NO: 61             moltype = AA  length = 17
```

```
FEATURE                 Location/Qualifiers
source                  1..17
                        mol_type = protein
                        organism = synthetic construct
SEQUENCE: 61
AIRWSDESPI YADSVKG                                                              17

SEQ ID NO: 62           moltype = AA  length = 17
FEATURE                 Location/Qualifiers
source                  1..17
                        mol_type = protein
                        organism = synthetic construct
SEQUENCE: 62
AIRWSGESPY YADSVKG                                                              17

SEQ ID NO: 63           moltype = AA  length = 16
FEATURE                 Location/Qualifiers
source                  1..16
                        mol_type = protein
                        organism = synthetic construct
SEQUENCE: 63
VISSSGSTNY ADSVKG                                                               16

SEQ ID NO: 64           moltype = AA  length = 19
FEATURE                 Location/Qualifiers
source                  1..19
                        mol_type = protein
                        organism = synthetic construct
SEQUENCE: 64
RLVPPGIPIE RSLENMNYW                                                            19

SEQ ID NO: 65           moltype = AA  length = 19
FEATURE                 Location/Qualifiers
source                  1..19
                        mol_type = protein
                        organism = synthetic construct
SEQUENCE: 65
RLVPPGIPIE RTLESMNYW                                                            19

SEQ ID NO: 66           moltype = AA  length = 19
FEATURE                 Location/Qualifiers
source                  1..19
                        mol_type = protein
                        organism = synthetic construct
SEQUENCE: 66
RLVPPGIPIE RTLESMRYW                                                            19

SEQ ID NO: 67           moltype = AA  length = 19
FEATURE                 Location/Qualifiers
source                  1..19
                        mol_type = protein
                        organism = synthetic construct
SEQUENCE: 67
RLVPPGIPIE RTLESMKDW                                                            19

SEQ ID NO: 68           moltype = AA  length = 19
FEATURE                 Location/Qualifiers
source                  1..19
                        mol_type = protein
                        organism = synthetic construct
SEQUENCE: 68
RLVPPGIPIP RTSESMRYW                                                            19

SEQ ID NO: 69           moltype = AA  length = 19
FEATURE                 Location/Qualifiers
source                  1..19
                        mol_type = protein
                        organism = synthetic construct
SEQUENCE: 69
RLVPPGIPIE RTLESMRYW                                                            19

SEQ ID NO: 70           moltype = AA  length = 19
FEATURE                 Location/Qualifiers
source                  1..19
                        mol_type = protein
                        organism = synthetic construct
SEQUENCE: 70
RLVPPGIPFE RTLENMRYW                                                            19
```

```
SEQ ID NO: 71           moltype = AA   length = 19
FEATURE                 Location/Qualifiers
source                  1..19
                        mol_type = protein
                        organism = synthetic construct
SEQUENCE: 71
RLVPPGIPIE RTLESMRYW                                                      19

SEQ ID NO: 72           moltype = AA   length = 19
FEATURE                 Location/Qualifiers
source                  1..19
                        mol_type = protein
                        organism = synthetic construct
SEQUENCE: 72
RLVPPGIPIE RTLESMNYW                                                      19

SEQ ID NO: 73           moltype = AA   length = 19
FEATURE                 Location/Qualifiers
source                  1..19
                        mol_type = protein
                        organism = synthetic construct
SEQUENCE: 73
RLVPPGIPIE RTLESMRYW                                                      19

SEQ ID NO: 74           moltype = AA   length = 19
FEATURE                 Location/Qualifiers
source                  1..19
                        mol_type = protein
                        organism = synthetic construct
SEQUENCE: 74
RLVPPGIPIE RTLENMRYS                                                      19

SEQ ID NO: 75           moltype = AA   length = 12
FEATURE                 Location/Qualifiers
REGION                  1..12
                        note = 3
source                  1..12
                        mol_type = protein
                        organism = synthetic construct
SEQUENCE: 75
TIPVPSTPYD YW                                                             12

SEQ ID NO: 76           moltype = AA   length = 19
FEATURE                 Location/Qualifiers
source                  1..19
                        mol_type = protein
                        organism = synthetic construct
SEQUENCE: 76
RLVPPGIPIE RTLENMNYW                                                      19

SEQ ID NO: 77           moltype = AA   length = 19
FEATURE                 Location/Qualifiers
source                  1..19
                        mol_type = protein
                        organism = synthetic construct
SEQUENCE: 77
RLVPPGIPIE RTLESMNYW                                                      19

SEQ ID NO: 78           moltype = AA   length = 19
FEATURE                 Location/Qualifiers
source                  1..19
                        mol_type = protein
                        organism = synthetic construct
SEQUENCE: 78
RLVPPGIPIE RTLESMKDW                                                      19

SEQ ID NO: 79           moltype = AA   length = 19
FEATURE                 Location/Qualifiers
source                  1..19
                        mol_type = protein
                        organism = synthetic construct
SEQUENCE: 79
RLVPPGIPIE RTLESMRYW                                                      19

SEQ ID NO: 80           moltype = AA   length = 19
FEATURE                 Location/Qualifiers
source                  1..19
                        mol_type = protein
                        organism = synthetic construct
```

```
SEQUENCE: 80
RLVPPGIPIG RTLESMNNW                                                              19

SEQ ID NO: 81          moltype = AA  length = 19
FEATURE                Location/Qualifiers
source                 1..19
                       mol_type = protein
                       organism = synthetic construct
SEQUENCE: 81
RLVPPGIPIE RALENMNYW                                                              19

SEQ ID NO: 82          moltype = AA  length = 19
FEATURE                Location/Qualifiers
source                 1..19
                       mol_type = protein
                       organism = synthetic construct
SEQUENCE: 82
RLVPPGIPIE RTLESMRYW                                                              19

SEQ ID NO: 83          moltype = AA  length = 19
FEATURE                Location/Qualifiers
source                 1..19
                       mol_type = protein
                       organism = synthetic construct
SEQUENCE: 83
RLVPPGIPIE RSLENMNYW                                                              19

SEQ ID NO: 84          moltype = AA  length = 11
FEATURE                Location/Qualifiers
source                 1..11
                       mol_type = protein
                       organism = synthetic construct
SEQUENCE: 84
HVAGFDEYNY W                                                                      11
```

SINGLE DOMAIN ANTIBODIES TARGETING CD1D

CROSS-REFERENCE TO RELATED APPLICATIONS

This application is a continuation of U.S. patent application Ser. No. 16/666,734, filed Oct. 29, 2019 (issued as U.S. Pat. No. 11,591,394), which is a continuation of U.S. patent application Ser. No. 15/546,406, filed Jul. 26, 2017 (issued as U.S. Pat. No. 10,501,541), which is a U.S. National Stage Application under 35 U.S.C. § 371 of International Application No. PCT/NL2016/050064, filed Jan. 27, 2016, which claims the benefit of the Netherlands Patent Application No. 2014192, filed Jan. 27, 2015, the disclosures of which are hereby incorporated by reference in their entireties for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LVAT_002_02US_SeqList_ST26.xml, Date created: Jun. 28, 2023, file size 77,002 bytes).

FIELD OF INVENTION

The present invention generally relates to the field of immunology, more in particular to the field of single-domain antibodies which bind to human CD1d, including antibodies that modify CD1d-mediated biological functions such as activation of CD1d-restricted T cells, including the natural killer T (NKT) cells, and modulation of the function of cells expressing CD1d. Provided are, for example, compounds which comprise at least one single-domain antibody which binds to CD1d, use of such compounds comprising at least one single-domain antibody and (pharmaceutical) compositions comprising such compounds.

BACKGROUND ART

CD1d is a member of the CD1 (cluster of differentiation 1) family of glycoproteins (including CD1a, CD1b, CD1c, CD1d and CD1e) expressed on the surface of various human cells, including antigen presenting cells (APC). In human CD1d is encoded by CD1D, also known as R3G1. APC displaying CD1d include Langerhans cells, (activated) B-cells, dendritic cells (e.g. in lymph nodes), and (activated) blood monocytes. CD1d is also expressed by various other cell types, for example in liver, pancreas, skin, kidney, uterus, conjunctiva, epididymis, thymus and tonsil (see, for example, Canchis et al. (1992) Immunology 80:561-565).

Cells that are activated/stimulated via CD1d include the Natural Killer T-cells (NKT cells). NKT cells are a heterogeneous group of T cells that share properties of both T cells and natural killer cells. NKT cells are a subset of T cells that express an alpha/beta T-cell receptor (TCR), as well a variety of molecular markers that are typically associated with NKT cells.

Type 1 or invariant NKT cells is the best-known group of NKT cells and differs from conventional αβ T cells in that their T-cell receptors are far more limited in diversity ('invariant'). The NKT cells, including these invariant and other CD1d-restricted T cells (type 2 NKT), recognize (self or foreign) lipids and glycolipids presented by CD1d molecules present on APC. The interaction between (lipid-presenting) CD1d and TCR triggers the release of cytokines including Th1- or Th2-like cytokines, such as interferon-gamma, tumor necrosis factor-alpha, and interleukins like IL-4, IL-5 and IL-13.

Different lipids have been shown to bind CD1d molecules, including mycolic acids, diacylglycerols, and sphingolipids. An alpha-galactosylceramide, KRN7000, is the best studied ligand of the lipid-binding CD1d in NKT cell activation in vitro and in vivo. Other ligands comprise isoglobotrihexosylceramide, (microbial-derived) glycuronosylceramides, alpha-C-galactosylceramides, threitol ceramide, and a variety of (human and non-human) glycolipids such as lysophophatidylcholine and lysosphingomyelin (see, for example, Fox et al (2009) PLOS Biology 7:10: e1000228).

Important roles of NKT cells have now been demonstrated in the regulation of autoimmune, allergic, antimicrobial, and antitumor immune responses (van der Vliet et al. (2004) Clinical Immunology 112(1): 8-23). Physiologically, the NKT-cells can augment or inhibit immune responses, including antitumor, autoimmune, and anti-pathogen responses, through a variety of mechanisms depending on context (Yue et al. (2010) The Journal of Immunology 184: 268-276), including induction of cell death in multiple myeloma cells. Conditions in which NKT-cells may be involved include autoimmune or inflammatory diseases, including myasthenia gravis, psoriasis, ulcerative colitis, primary biliary cirrhosis, colitis, autoimmune hepatitis, atherosclerosis, and asthma. In addition to cytokine release, NKT cell effector functions which result in cell lysis, such as perforin release and granzyme release and cell death, may also be relevant in conditions in which NKT cells are implicated, such as in cancer. Modulation of CD1d-mediated effects is therefore of potential therapeutic benefit.

There is an ongoing need for compounds that can bind and/or interact with CD1d as specific as possible, i.e. while minimally or not binding to other family members of the CD1-family, both in vitro and in vivo. In particular there is need for such compounds that bind and/or modulate (activate or inhibit) biological functions that involve CD1d such as, but not limited to, NKT-cell activation. Such compounds may, for example, show benefit in the various diseases in which CD1d-mediated functions play a role.

SUMMARY OF THE INVENTION

The present invention provides a compound comprising at least one single-domain antibody. The single-domain antibody binds to human CD1d. The single-domain antibody that binds to human CD1d comprises a CDR1, CDR3 and CDR3 region with an amino acid sequence as disclosed herein, and conservative sequence variants thereof.

Preferably the single-domain antibody has a CDR1, CDR2 and CDR3 region in the combination as disclosed herein, for example as shown in Table 1.

Even more preferably, the single domain antibody has an amino acid sequence selected from the group of SEQ ID NO: 1-SEQ ID NO: 21.

The compound according to the invention may be any kind of compound, for example a complex, as long as the single-domain antibody that binds to human CD1d is comprised in the compound. Preferably the compound is a polypeptide. In certain embodiments the compound may consist of only the single-domain antibody that binds to human CD1d. In other embodiments the compounds consists of the single-domain antibody that binds to human CD1d and a label. In even further embodiments the compound may comprise the single-domain antibody that binds to human CD1d linked to a pharmaceutical active agent and/or other antibodies.

Also provided is use of the compound according to the invention in medical treatment and/or as a diagnostic agent.

Also provided is a pharmaceutical composition that comprises a compound as disclosed herein and nucleotide sequences and host cells comprising such nucleotide sequences that encode for the compounds according to the invention.

BRIEF DESCRIPTION OF THE DRAWINGS/FIGURES

FIG. 1: CD1d-specificity of individual selected nanobodies. Flow-cytometry was used to detect binding of isotype control mAb (IgG2b), anti-CD1d 51.1 mAb, R2 negative control VHH, and individual CD1d-specific VHH. Data demonstrate binding to CD1a, CD1b, CD1c, and CD1d transfected tumor cell lines (n=3).

Figure 2:
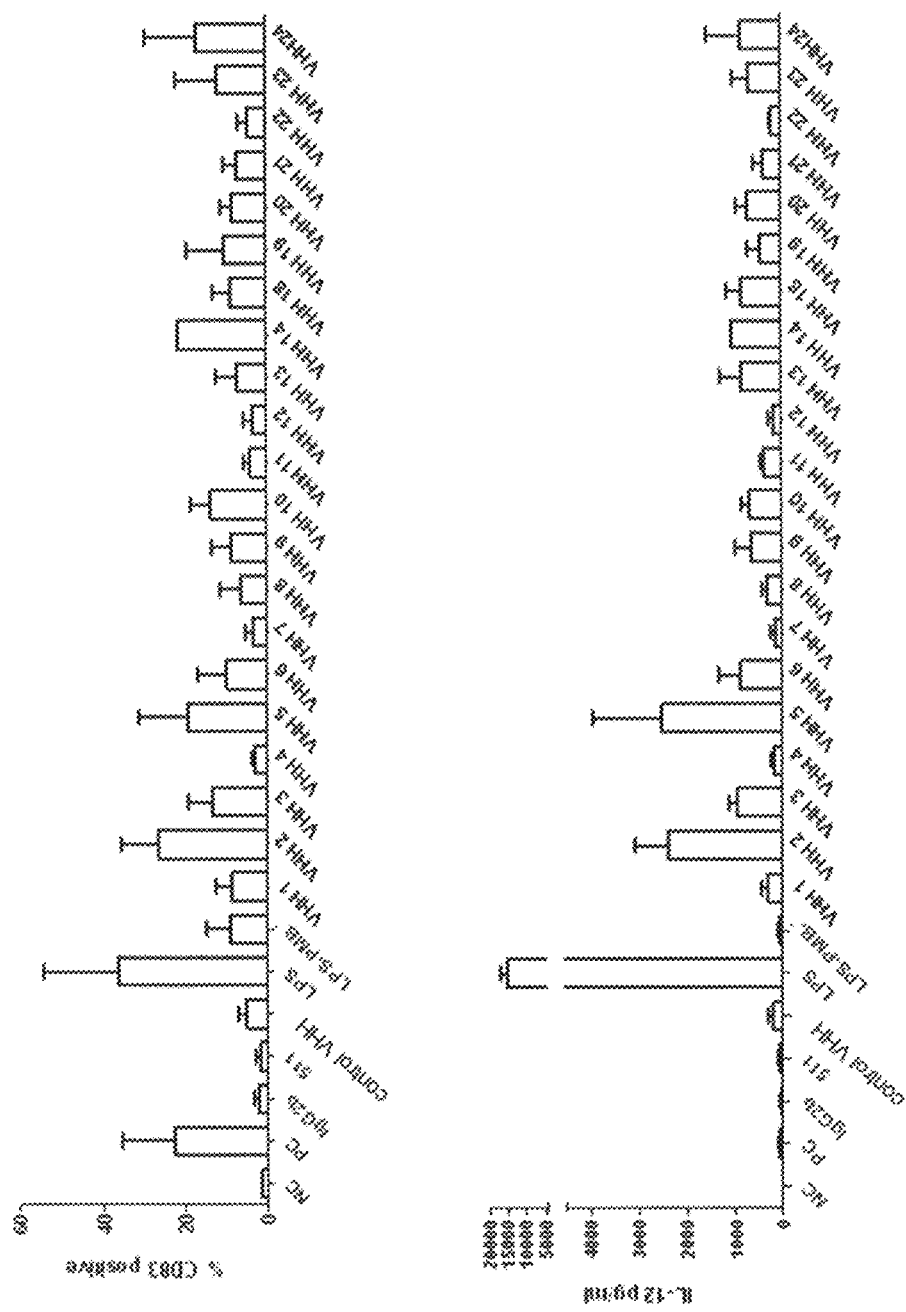

FIG. 2: Induction of moDC maturation and cytokine production by CD1d-specific nanobodies. Immature moDC were cultured with CD1d-specific nanobodies. After 24 hours, supernatants were harvested for detection of cytokine production (ELISA). After 72 h, moDC were analyzed for cell surface expression of the maturation marker CD83 using flow cytometry. NC=negative control, PC=positive control, IgG2b=isotype control mAb, 51.1=anti-CD1d 51.1 mAb, LPS=lipopolysaccharide, LPS-PMB=lipo-polysaccharide with polymyxin B. Data represent mean+SEM, n=3.

Figure 3:
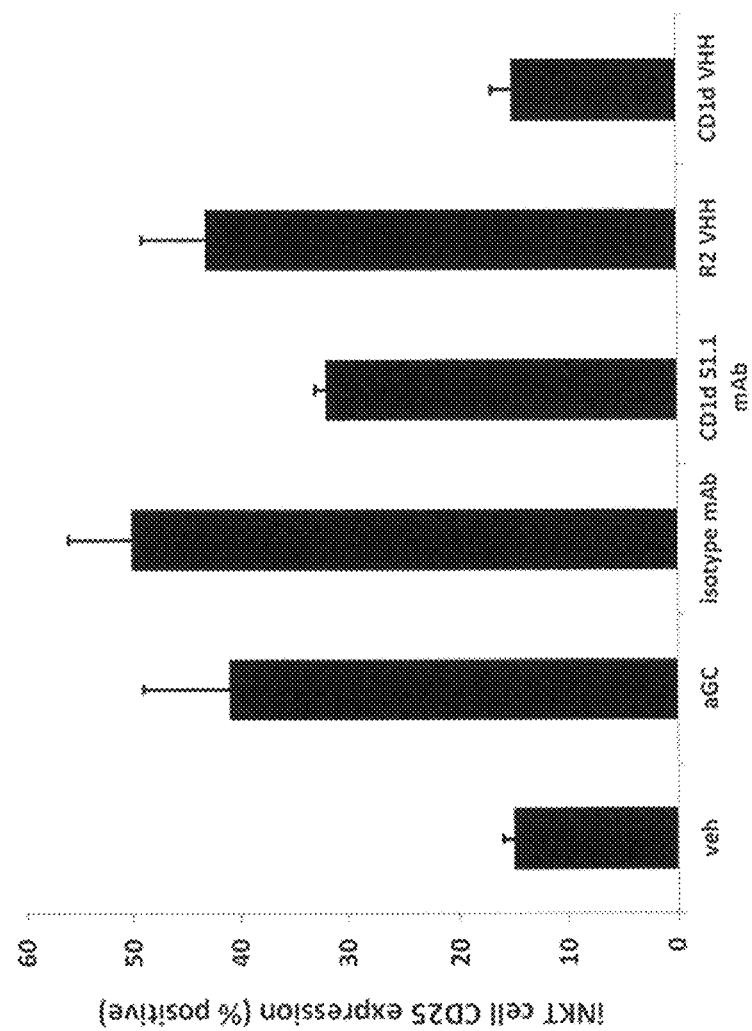

FIG. 3: Inhibition of α-GalCer induced iNKT cell activation. CD1d-transfected HeLa cells were pulsed overnight with vehicle control (veh) or α-GalCer (all other conditions). After washing, vehicle or α-GalCer pulsed HeLa-CD1d were cultured for 2 hours with IgG2b isotype control mAb, anti-CD1d 51.1 mAb, negative control VHH R2, or a neutralizing anti-CD1d VHH (VHH 24 (18-29c)) after which time iNKT cells were added. After 24 hr iNKT cell activation (CD25 expression) was determined using flow cytometry. Data indicate mean+SEM of 3 experiments. Superior neutralization of iNKT cell activation by anti-CD1d VHH.

Figure 4:
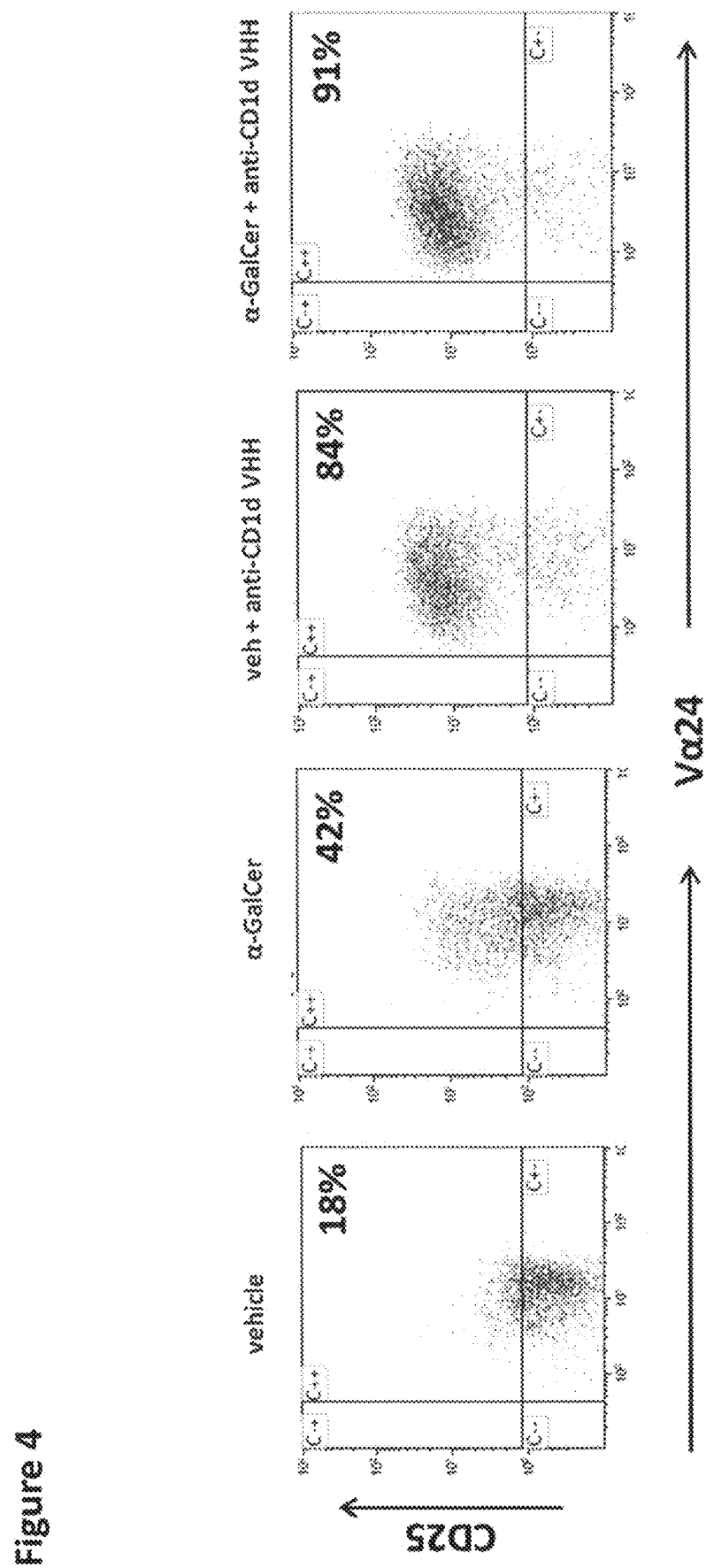

FIG. 4: Induction of iNKT cell activation. CD1d-transfected C1R cells were pulsed overnight with vehicle control (veh) or α-GalCer as indicated. After washing, vehicle or α-GalCer pulsed C1R-CD1d were cultured for 2 hours with or without a specific anti-CD1d VHH after which iNKT cells were added. After 24 hr iNKT cell activation (CD25 expression) was determined using flow cytometry. Representative flow cytometric dotplots demonstrating activation of iNKT cells by α-GalCer, but more strikingly after co-culture with the anti-CD1d VHH (VHH12 (18-14b)). Data are representative from multiple experiments with multiple CD1d-expressing tumor cell lines.

Figure 5:
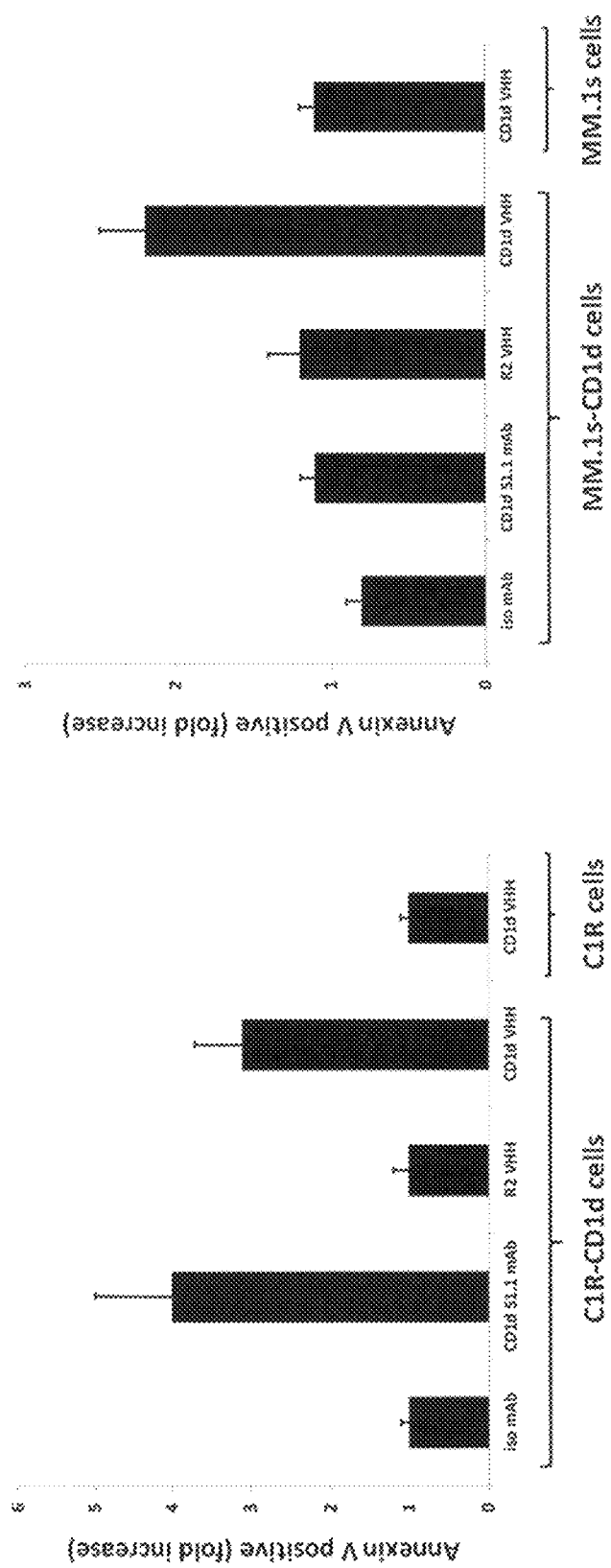

FIG. 5: Induction of annexin V binding by anti-CD1d nanobodies. C1R cells, CD1d-transfected C1R cells (left panel) and MM.1s cells and CD1d-transfected MM.1s cells (right panel) were cultured for 24 hours with IgG2b isotype control mAb, anti-CD1d 51.1 mAb, negative control VHH R2, or a CD1d-specific VHH (VHH19 (19-23G)). Percentage of target cells binding annexin V, which is suggestive of early apoptosis, was then determined by flow-cytometry. Data indicate mean+SEM of 3 experiments.

Figure 6:
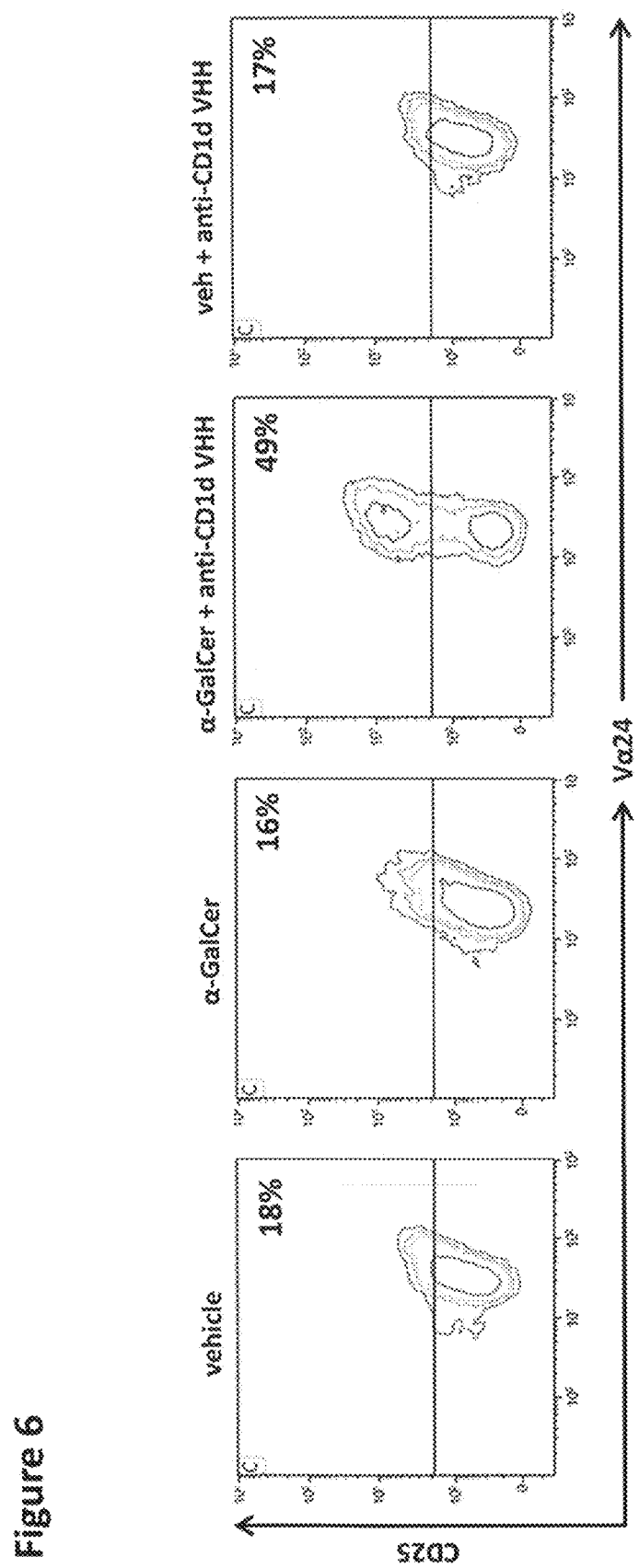

FIG. 6: Induction of iNKT cell activation using plate-bound β2m-human CD1d (±vehicle, α-GalCer and/or anti-CD1d VHH). 96-well plates were coated with a bispecific construct consisting of anti-EGFR VHH fused to β2m-hCD1d (loaded with either vehicle control or α-GalCer). Coated plates were cultured for 2 hours in the presence or absence of an anti-CD1d VHH (VHH12) after which iNKT cells were added. After 24 hours iNKT cell activation (CD25 expression) was determined using flowcytometry. Representative flowcytometric dotplots demonstrating slight activation of iNKT cells by α-GalCer-loaded β2m-hCD1d, but robust activation after co-culture of α-GalCer-loaded β2m-hCD1d with the anti-CD1d VHH (VHH12 (18-14b)).

Figure 7:
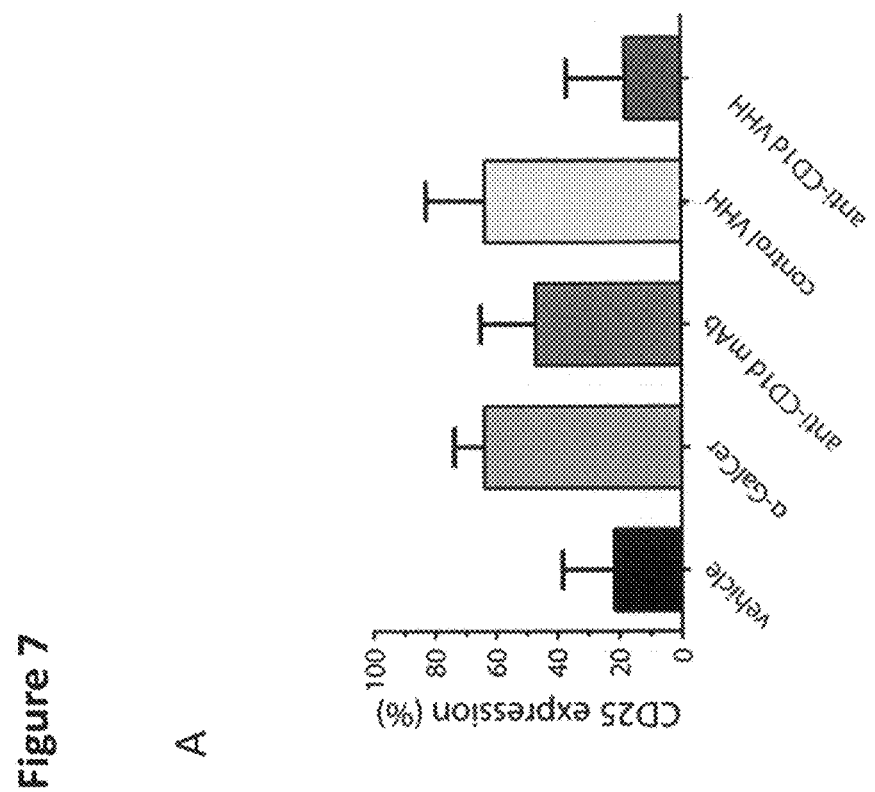
Figure 7:
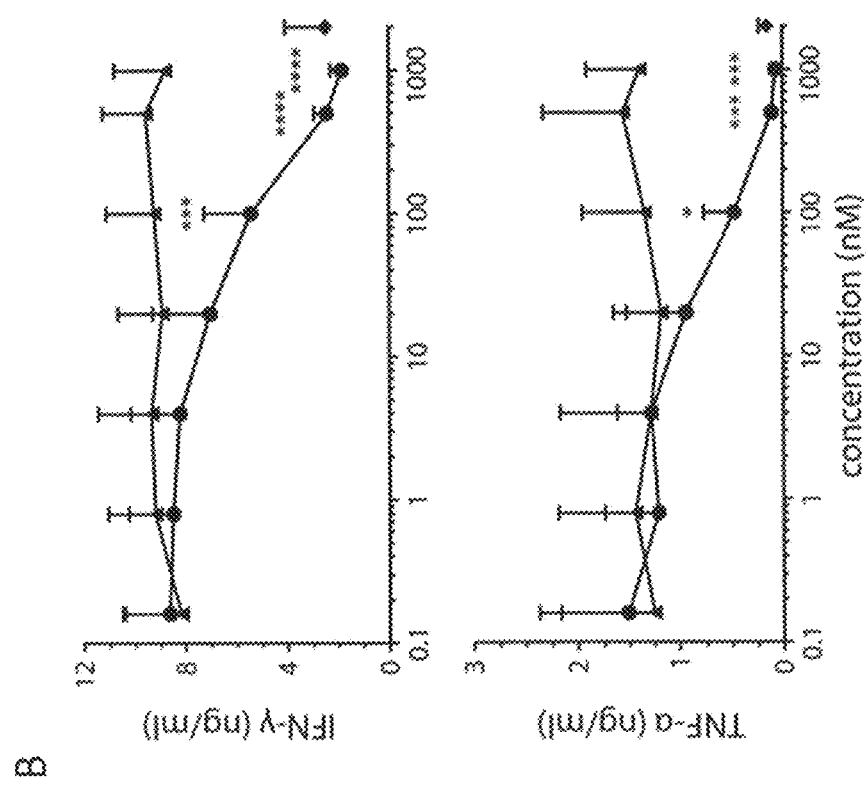

FIG. 7: Dose dependent inhibition of CD1d-α-GalCer mediated iNKT cell activation. iNKT CD25 expression, IFN-γ and TNF-α production were determined after a 24 h co-culture of iNKT with CD1d-transfected HeLa cells pulsed with vehicle control (vehicle) or α-GalCer (all other conditions) and medium (vehicle and α-GC), anti-CD1d mAb 51.1 (10 µg/ml), control VHH (500 nM) or anti-CD1d VHH (VHH24; 500 nM). Graphical representation showing CD25 expression on iNKT cells (a). Concentration dependent effect of anti-CD1d VHH (● symbols) and a control non-inhibitory but CD1d-specific VHH (▲ symbols) on IFN-γ and TNF-α production. ♦ indicate the vehicle loaded control condition (b). Mean+SD, n=3, p<0.05, p<0.01, ****p<0.0001. The tested VHH is VHH24.

Figure 8:
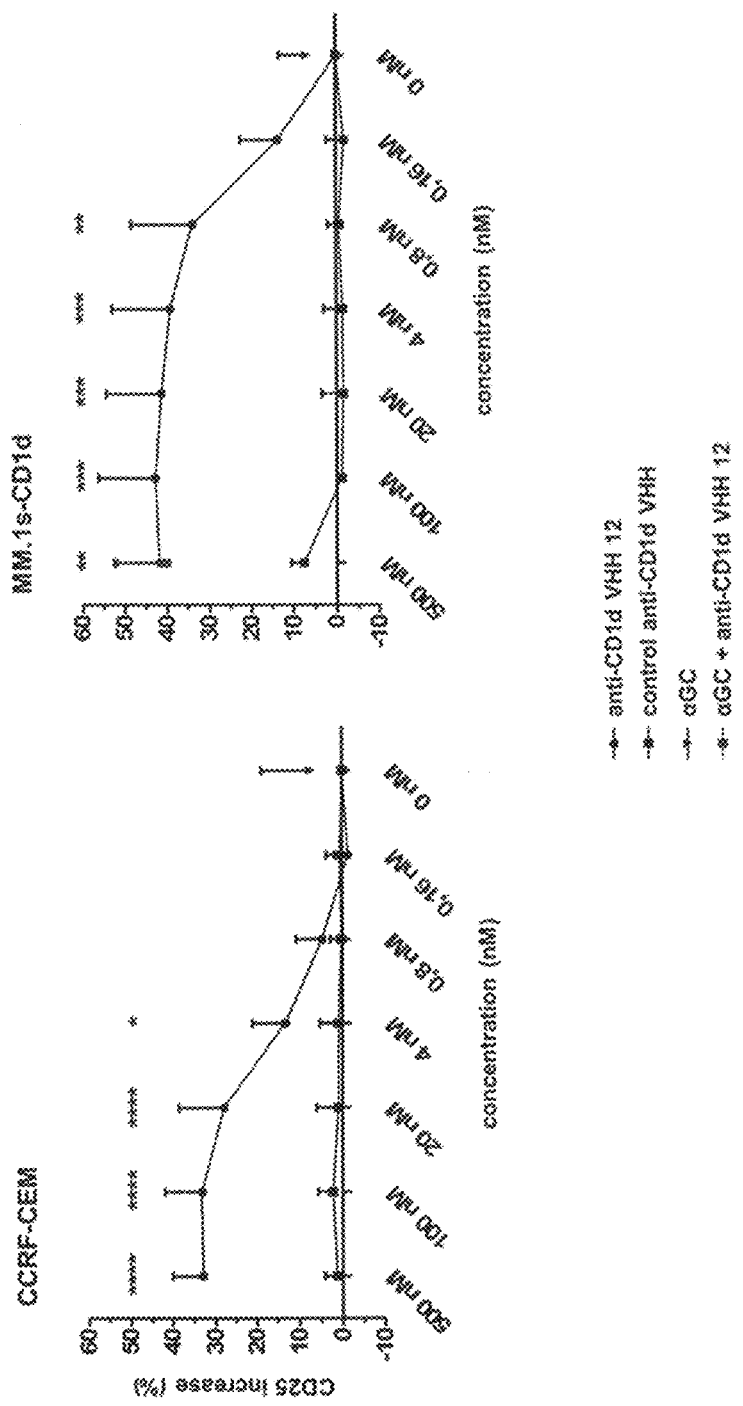

FIG. 8: Dose dependent iNKT cell activation by anti-CD1d VHH12. CCRF-CEM (T-ALL, CD1d positive; n=4) and CD1d-transfected MM.1s (multiple myeloma; n=3) cells were pulsed with vehicle control or αGC, incubated with anti-CD1d VHH and controls and co-cultured with iNKT for 24 h after which iNKT CD25 expression was determined. *p<0.05, p<0.01, *p<0.001, ****p<0.0001 (compare to FIG. 4).

Figure 9:
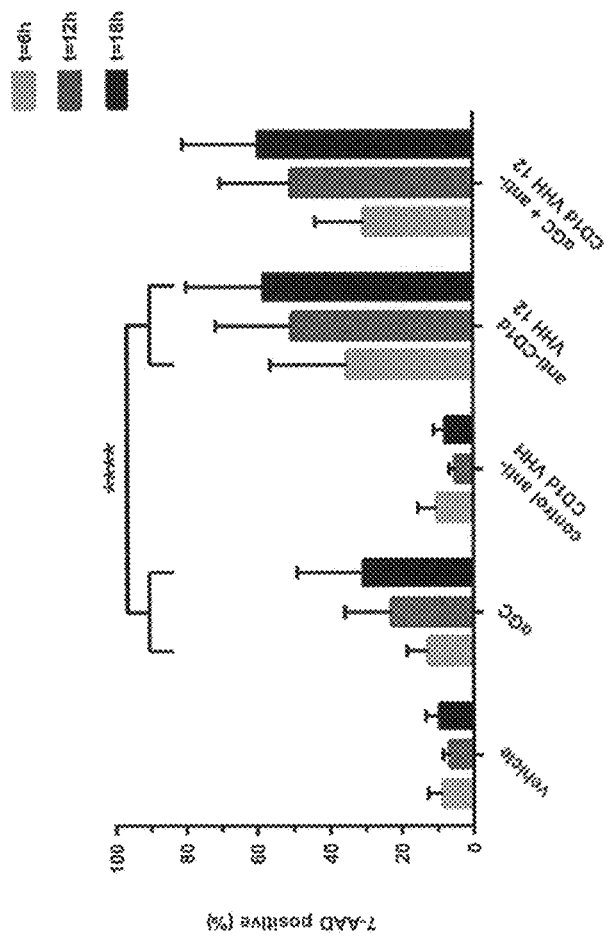
Figure 9:
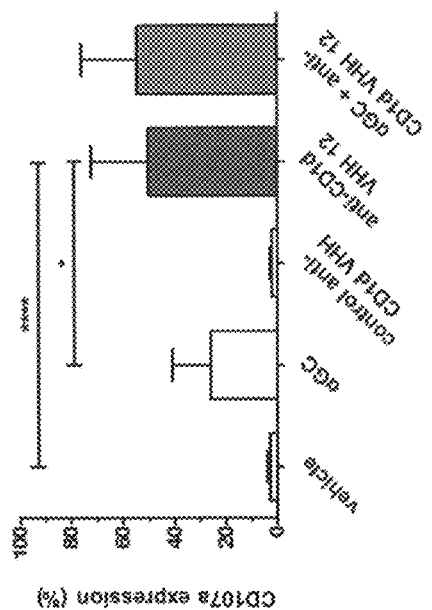

FIG. 9: Induction of iNKT cell degranulation (left) and cytotoxicity against CD1d+ tumor cells line (right). CCRF-CEM cells (CD1d-positive) were pulsed with vehicle control or αGC, incubated with anti-CD1d VHH and controls and co-cultured with iNKT (E:T ratio of 1:2) for the indicated time 6, 12 or 18 h) and stained with CD107a (t=4 h) or annexin V and 7-AAD for flow cytometry. N=5; *p<0.05; ***p<0.001. The anti-CD1d VHH shown is VHH12.

Figure 10:
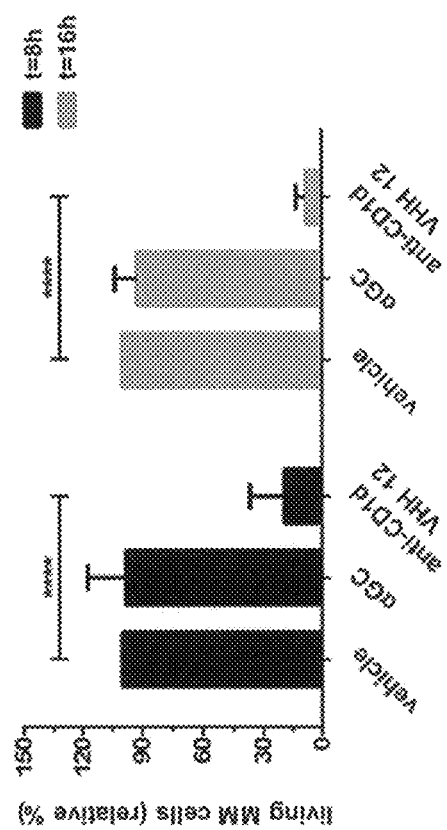

FIG. 10: Induction of iNKT cell cytotoxicity against CD1d+ primary multiple myeloma cells. Thawed primary bone marrow samples from MM patients were pulsed with vehicle control or αGC or incubated with anti-CD1d VHH and controls and then co-cultured with iNKT for the indicated time (8 and 16 h) after which the percentage of surviving MM cells was determined. The anti-CD1d VHH shown is VHH12.

Figure 11:
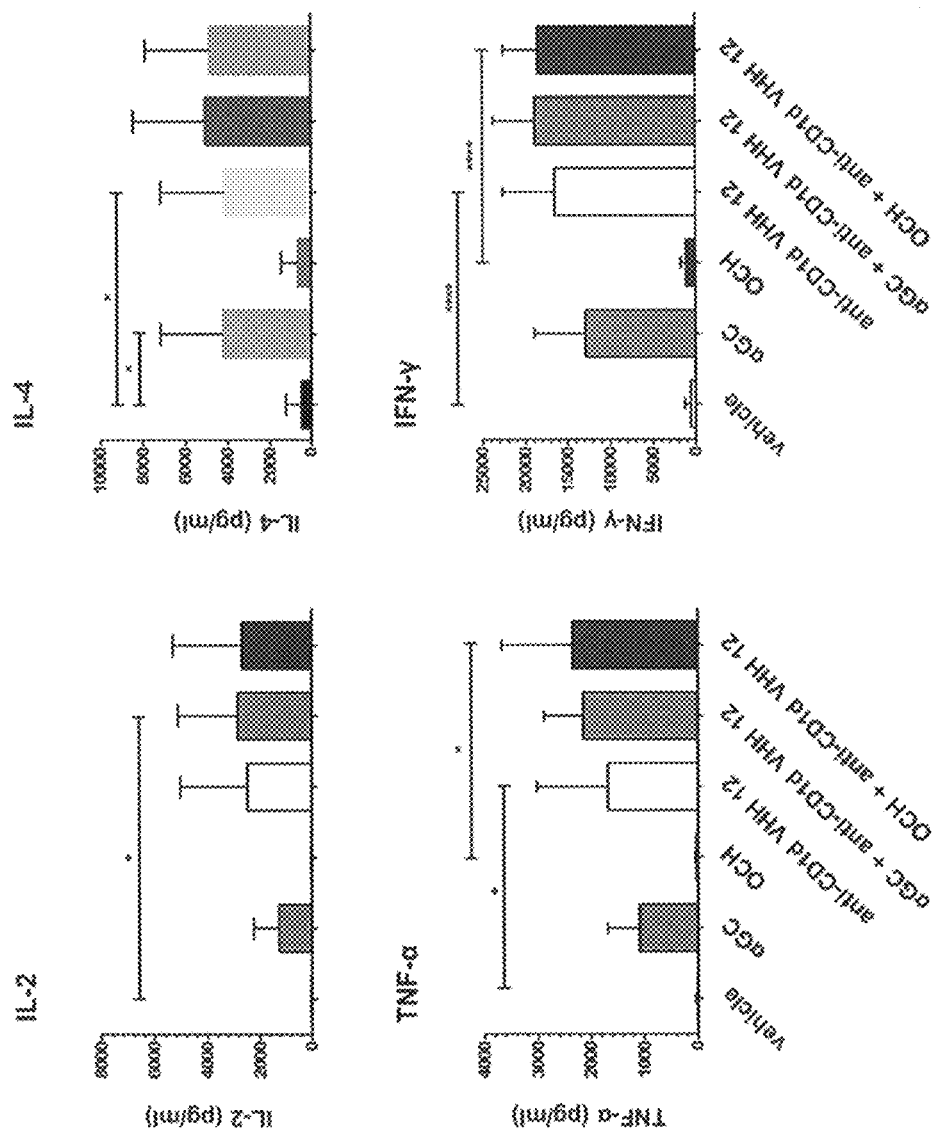

FIG. 11: Induction of iNKT cell cytokine production by anti-CD1d VHH12. For detection of cytokine production HeLa-CD1d cells were pulsed with vehicle control, OCH (a sphingosine truncated analog of alpha-galactosylceramide (alpha-GC); glycolipid reported to induce Th2-cytokine production in iNKT cells) or αGC, incubated with anti-CD1d VHH and controls and co-cultured with iNKT for 24 h after which supernatants were analyzed (by Cytometric Bead Assay; CBA). N=4; *p<0.05; ****p<0.0001.

DETAILED DESCRIPTION OF THE INVENTION

Definitions

In the following description and examples a number of terms are used. In order to provide a clear and consistent understanding of the specifications and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed in handbooks.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for using "a" compound, includes using a plurality of this compound (e.g. 10s, 100s, 1000s, 10s of thousands, 100s of thousands, millions, or more molecules).

With the term "aligning" and "alignment" is meant the comparison or amino acid sequences of two or more molecules/compounds based on the presence of short or long stretches of identical or similar amino acids. Several methods for alignment of amino acid sequences are known in the art, as will be further explained below.

"Sequence identity" is a measure of the identity of nucleotide sequences or amino acid sequences. In general, the sequences are aligned so that the highest order match is obtained. "Identity" per se has an art-recognized meaning and can be calculated using published techniques. Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity may be codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403). Sequence identity as disclosed herein was determined by calculating) the percentage of amino acids that are similar (number of amino acids similar to reference sequence divided by total number of amino acids in the reference sequence), essentially as outlined in the paragraph below.

As an illustration, by an amino acid sequence with at least, for example, 70% "sequence identity" to a reference amino acid sequence of SEQ ID NO: 1 it is intended that the amino acid sequence is identical to the reference sequence except that the polypeptide sequence may include up to 3 amino acid alterations per each of the 10 amino acids of the reference amino acid of SEQ ID NO: 1. Hence, the percentage of identity of an amino acid sequence to a reference amino acid sequence is to be calculated over the full length of the reference amino acid sequence. In other words, to obtain an amino acid sequence comprising at least 70% identical to a reference amino acid sequence, up to 30% of the amino acid residues in the reference sequence may be deleted or substituted with another amino acid, or a number of amino acids up to 30% of the total amino acid residues in the reference sequence may be inserted into the reference sequence. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

The terms "amino acid sequence" or "protein" or "peptide" refer to molecules consisting of a chain of amino acids, without reference to a specific mode of action, size, 3 dimensional structure or origin. A "fragment" or "portion" of thereof may thus still be referred to as an "amino acid sequence" or "protein" or "peptide". An "isolated amino acid sequence" is used to refer to an amino acid chain with a particular sequence and which is no longer in its original natural environment, for example in vitro or in a recombinant bacterial or human host cell.

Each immunoglobulin molecule has a variable domain. The variable domain of immunoglobulin molecules is subdivided into hypervariable (HV) and framework (FR) regions. HV regions have a high ratio of different amino acids in a given position, relative to the most common amino acid in that position. The hypervariability regions are referred to as complementarity determining regions (CDR). Immunoglobulin molecules have three complementarity determining regions (CDR1, CDR2 and CDR3). Four framework regions, with much less variable amino acids sequences, separate the CDR regions. The CDR regions can direct binding to the antigen, such as CD1d.

Description

The present invention generally relates to compounds comprising single-domain antibodies which bind to human CD1d. The present inventors have found single-domain antibodies and antigen-binding portions thereof which bind to human CD1d.

In a first aspect there is provided for a compound comprising at least one single-domain antibody which binds to human CD1d, wherein the single-domain antibody comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

As disclosed before, CD1d (Entrez Gene ID 912; NCBI Reference Sequence: NP_001757; Balk et al. (1989) Proc Natl Acad Sci USA 86:252-256) is expressed in a variety of cells including B-cells in chronic lymphocytic leukemia patients, hepatocytes, dendritic cells, and tumor cells and the single-domain antibodies disclosed herein can be used for binding to CD1d, for example, but not restricted to binding to CD1d on any of these cells or for binding to CD1d on other cells expressing CD1d, or for binding to CD1d molecules that are not bound to cells, and that are either not bound to anything, or are for example linked to or associated with carriers, polymers or other proteins.

The compound comprising the single-domain antibody which binds human CD1d can be any kind of compound or complex as long as it comprises a single-domain antibody which binds to CD1d. Preferably, the compound according to the invention can bind human CD1d due to the presence of the single-domain antibody which binds human CD1d.

The compound according to the invention may further comprise other function or non-functional groups. For example, the single-domain antibody of the current invention may be linked to a nanoparticle, a liposome, a virus, a label, another antibody or protein structure (e.g. a receptor) or may be fused to an antigen, peptide, a drug, a marker, or nucleic acid. For example, the compound may also comprise a magnetic bead, allowing the isolation of CD1d expressing cells.

The CD1d single-domain antibody may be linked via the carboxyl or amino terminus of the antibody, or may be linked at a site other than the carboxyl or amino termini. The attachment to the CD1d single-domain antibody may be direct, i.e., without any intermediate sequence, or through a linker amino acid sequence, a linker molecule, or a chemical bond. For example, the coupling may be of a physical and/or chemical type.

In one embodiment, the compound is a bi-specific antibody or a multi-specific antibody. In one embodiment, the compound is a bivalent antibody or a multivalent antibody. Bivalency or multi-valency can allow antibodies to bind to multimeric antigen with great avidity; bi-specificity or multi-specificity can allow the cross-linking of two antigens.

The compound comprises at least one single-domain antibody which binds to human CD1d, wherein the single-domain antibody comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

Single domain antibodies (sdAb, also called Nanobody by Ablynx, the developer, or VHH) are well known to the skilled person. Single domain antibodies are antibodies whose complementarity determining regions are part of a single domain polypeptide. Single domain antibodies thus comprise a single complementarity determining region (CDR) 1 (CDR1), a single CDR2 and a single CDR3. Examples of single domain antibodies are heavy chain only antibodies, antibodies that naturally do not comprise light chains, single domain antibodies derived from conventional antibodies, and engineered antibodies.

Single domain antibodies may be derived from any species including mouse, human, camel, llama, goat, rabbit, and bovine. For example, naturally occurring VHH molecules can be derived from antibodies raised in Camelidae species, for example in camel, dromedary, alpaca and guanaco.

Like a whole antibody, a single domain antibody is able to bind selectively to a specific antigen. Single domain antibodies may contain only the variable domain of an immunoglobulin chain having CDR1, CDR2 and CDR3 and framework regions. With a molecular weight of only about 12-15 kDa, nanobodies are much smaller than common antibodies (150-160 kDa) which are composed of two heavy chains and two light chains.

CDR1, CDR2 and CDR3 sequences may be exchanged between species. For example, from a llama immunoglobulin molecule, CDR sequences may be selected and exchanged with CDR sequences in a human immunoglobulin molecule, to obtain a human immunoglobulin molecule having the specificity that is derived from the llama CDR sequences. This may be advantageous as a human sequence may be less immunogenic to humans as compared to the original llama framework sequence. Such an exchange of CDR sequences is known as humanization.

Hence, the immunoglobulin molecules according to the invention may have human derived immunoglobulin sequences or llama derived immunoglobulin sequences and have the CDR1, CDR2 and CDR3 sequences replaced with the CDR sequences according to the invention in order to provide for human CD1d binding. In other words, the compound according to the invention may comprise a humanized single-domain antibody with CDRs as disclosed herein. For example, a single domain antibody may have human framework sequences and CDR regions as disclosed herein.

The single-domain antibody that is comprised in the compound according to the invention comprises complementarity determining regions CDR1, CDR2 and CDR3, wherein CDR1 comprises an amino acid sequence that has at least 60% sequence identity with SEQ ID NO: 22 and CDR2 comprises an amino acid sequence that has at least 60% sequence identity with SEQ ID NO: 43.

The sequence of SEQ ID NO:22 correspond with the sequence of CDR1 of the single-domain antibody denoted as 17-1E in Table 1 herein. For the purpose of the current invention the single-domain antibody 17-1E may also be referred to as VHH number 1. The sequence of the single-domain antibody 17-1E is shown as SEQ ID NO:1 and comprises, in addition to the sequences of the CDR1, CDR2 and CDR3 as shown in Table 1 also the framework sequences.

The sequence with SEQ ID NO:43 correspond with the sequence of CDR2 of the single-domain antibody denoted as 17-1E in Table 1 herein.

For all single-domain antibodies described herein and, for example, as listed in Table 1, the region before CDR1 may be referred to as framework region (FW) 1, the region between CDR1 and CDR2 may be referred to as FW2, the region between CDR2 and CDR3 may be referred to as FW3, and the region after CDR3 may be referred to as FW4. The respective individual framework regions FW1, FW2, FW3 or FW4 can be easily established based on the sequences of the CDR1, CDR2 and CDR3 and the whole single-domain antibody, and are therefore disclosed as such.

It was surprisingly found that a variety of single-domain antibodies could be obtained that share a high amino acid sequence identity with respect to the CDR1 and CDR2 of the various single-domain antibodies. The CDR1, CDR2 and CDR3 sequences of the single-domain antibodies found are listed in Table 1. For example, the single-domain antibody denoted as 19-23G in Table 1 has VHH number 19, and has a combination of a CDR1 with a sequence that corresponds with SEQ ID NO:37, a CDR2 with a sequence that corresponds with SEQ ID NO: 58 and a CDR3 with a sequence that corresponds with SEQ ID NO: 79. The whole sequence, including framework regions of this VHH is SEQ ID NO: 16.

However, according to the invention the single-domain antibody may comprise any combination of a CDR1, CDR2 and CDR3 as long as CDR1 shows at least 60% sequence identity with SEQ ID NO: 22 and CDR2 comprises an amino acid sequence that has at least 60% sequence identity with SEQ ID NO: 43. For example, also contemplated is that the single-domain antibody comprises a CDR1 as shown in Table 1 of a first VHH (for example VHH nr 10) and a CDR2 as shown in Table 1 of a second VHH (for example VHH nr 20).

In other words, it will be appreciated that, based on the present disclosure, the skilled person can, without undue burden, provide compounds according to the invention, comprising at least one single-domain antibody which binds to human CD1d, wherein the CDR1 of the single-domain antibody comprises an amino acid sequence that has at least 60% sequence identity with SEQ ID NO: 22 and the CDR2 of the single-domain antibody comprises an amino acid sequence that has at least 60% sequence identity with SEQ ID NO: 43. For example, based on the various CDR1s and CDR2 shown in Table 1.

In a preferred embodiment CDR1 over its entire length shows at least 60% sequence identity with SEQ ID NO: 22. In a preferred embodiment CDR2 over its entire length shows at least 60% sequence identity with SEQ ID NO: 43. Preferable, CDR1 over its entire length shows at least 60% sequence identity with SEQ ID NO: 22 and CDR2 over its entire length shows at least 60% sequence identity with SEQ ID NO: 43. Preferably CDR1 and/or CDR2 shows at least 65%, 70%, 75%, 80%, 90%, 95%, 97%, 99% identity with respectively SEQ ID NO:22 and/or SEQ ID NO: 43.

Also provided is a compound comprising at least one single-domain antibody which binds to human CD1d, wherein the single-domain antibody comprises complementarity determining regions CDR1, CDR2 and CDR3 and wherein CDR1 comprises an amino acid sequence that has at least 90% sequence identity with SEQ ID NO: 22, CDR2 comprises an amino acid sequence that has at least 80% sequence identity with SEQ ID NO: 43, and CDR3 comprises an amino acid sequence that has at least 70% sequence identity with SEQ ID NO: 64; or wherein CDR1 comprises an amino acid sequence selected from the group consisting of SEQ ID NO: 33 and SEQ ID NO: 42, CDR2 comprises an amino acid sequence selected from the group consisting of SEQ ID NO: 54 and SEQ ID NO: 63 and CDR3 comprises an amino acid sequence selected from the group consisting of SEQ ID NO: 75 and SEQ ID NO: 84.

It was found that within the provided single-domain antibodies that can be comprised in the compound according to the present invention, a group is present that displays for the CDR1 an amino acid sequence that has at least 90% sequence identity with SEQ ID NO: 22, for the CDR2 an amino acid sequence that has at least 80% sequence identity with SEQ ID NO: 43 and for the CDR3 an amino acid sequence that has at least 70% sequence identity with SEQ ID NO: 64. These single-domain antibodies share a high degree of identity with respect to the respective complementarity determining regions. In a preferred embodiment CDR1 over its entire length shows at least 90% sequence identity with SEQ ID NO: 22. In a preferred embodiment CDR2 over its entire length shows at least 80% sequence identity with SEQ ID NO: 43. In a preferred embodiment CDR3 over its entire length shows at least 70% sequence identity with SEQ ID NO: 64. Preferable, CDR1 over its entire length shows at least 90% sequence identity with SEQ ID NO: 22, CDR2 over its entire length shows at least 80% sequence identity with SEQ ID NO: 43 and CDR3 over its entire length shows at least 70% sequence identity with SEQ ID NO: 64. Preferably CDR1 shows at least 90%, 92%, 95%, 97%, 99% identity with SEQ ID NO:22, CDR2 shows at least 80%, 82%, 85%, 90%, 92%, 95%, 97%, 99% identity with SEQ ID NO: 43 and CDR3 shows at least 70%, 72%, 75%, 78%, 80%, 82%, 85%, 90%, 92%, 95%, 97%, 99% identify with SEQ ID NO: 64.

According to the invention, in a preferred embodiment, the single-domain antibody may comprise any combination of a CDR1, CDR2 and CDR3 as long as CDR1 shows at least 90% sequence identity with SEQ ID NO: 22 and CDR2 comprises an amino acid sequence that has at least 80% sequence identity with SEQ ID NO: 43 and CDR3 comprises an amino acid sequence that has at least 70% identity with SEQ ID NO:64. For example, also contemplated is that the single-domain antibody comprises a CDR1 as shown in Table 1 of a first VHH (for example VHH nr 10; SEQ ID NO: 31) and a CDR2 as shown in Table 1 of a second VHH (for example VHH nr 20; SEQ ID NO: 59), and a CDR3 as shown in Table 1 of the first or second VHH or of a third VHH (for example VHH nr 21; SEQ ID NO: 81).

In other words, it will be appreciated that, based on the present disclosure, in a preferred embodiment, the skilled person can, without undue burden, provide compounds according to the invention, comprising at least one single-domain antibody which bind to human CD1d by combining different CDR1, CDR2 and CDR3's, wherein the CDR1 of the single-domain antibody comprises an amino acid sequence that has at least 90% sequence identity with SEQ ID NO: 22 and the CDR2 of the single-domain antibody comprises an amino acid sequence that has at least 80% sequence identity with SEQ ID NO: 43 and the CDR3 of the single-domain antibody comprises an amino acid sequence that has at least 70% sequence identity with SEQ ID NO: 64. For example, based on the various CDR1, CDR2 and CDR3 shown in Table 1.

In another preferred embodiment, there is provided a compound comprising at least one single-domain antibody which binds to human CD1d, wherein the single-domain antibody comprises complementarity determining regions CDR1, CDR2 and CDR3 wherein CDR1 comprises an amino acid sequence selected from the group consisting of SEQ ID NO: 33 and SEQ ID NO: 42, CDR2 comprises an amino acid sequence selected from the group consisting of SEQ ID NO: 54 and SEQ ID NO: 63 and CDR3 comprises an amino acid sequence selected from the group consisting of SEQ ID NO: 75 and SEQ ID NO: 84.

Preferably, there is provided for compound comprising at least one single-domain antibody which binds to human CD1d as disclosed herein, wherein the single-domain antibody has complementarity determining regions CDR1, CDR2 and CDR3 as listed in combination in Table 1, or conservative sequence variants thereof.

Although it will be appreciated that the skilled person will be able to provide for various single-domain antibodies based on the various CDR1, CDR2, CDR3 as disclosed herein, as well as the other sequences provided (including the various framework sequences and the full-length sequence of the single-domain antibodies), preferably the single-domain antibody has a CDR1, CDR2 and a CDR3 as shown in combination in Table 1, and conservative sequence variants thereof. In other words, a compound according to the invention comprises a single-domain antibody wherein, preferably, the CDR1 and the CDR2 and the CDR3 are of one and the same VHH as shown in Table 1. For example, the single-domain antibody has the CDR1, CDR2 and CDR3 of the same VHH as shown in Table 1, for example of VHH1, VHH2, VHH3 . . . VHH14, VHH18, VHH 19 . . . VHH24. It was found that in particular CDR1, CDR2 and CDR3 as shown in combination (i.e. from the same VHH) show beneficial CD1d binding. As will be appreciated by the skilled person, also included are conservative sequence variants of the CDR1, CDR2 and CDR3 combinations as disclosed in Table 1.

Indeed in determining the degree of sequence identity between two amino acid sequences or in establishing the CDR1, CDR2 and CDR3 combination in the single-domain antibody, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, WO 00/46383, WO 01/09300 and WO 04/037999. Conservative substitutions preferably are substitutions in which one amino acid within the following groups (a)-(e): An amino acid residue is substituted by another amino acid residue within the same group (a)-(e): (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Preferred examples of conservative substitutions are as follows: Ala into Gly or into Ser; Arg into Lys; Asn into Gln or into His; Asp into Glu; Cys into Ser, Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr, Ser into Thr; Thr into Ser, Trp into Tyr; Tyr into Trp; and/or Phe into Val, into Ile or into Leu.

Preferably, the single-domain antibody has complementarity determining regions CDR1, CDR2 and CDR3 as listed in combination in Table 1, including conservative sequence variants thereof. More preferably, the single-domain antibody has complementarity determining regions CDR1, CDR2 and CDR3 as listed in combination in Table 1.

Also provided is a compound as disclosed herein and above wherein the compound comprises an amino acid sequence selected from the group consisting of SEQ ID NO: 1-SEQ ID NO: 21, or conservative sequence variants thereof.

In other words, preferably, the single-domain antibody comprised in the compound according to the invention comprises or consists of an amino acid sequence selected from the group consisting of SEQ ID NO: 1-SEQ ID NO: 21, or, as explained above, conservative sequence variants thereof. These sequences 1-22 represent single-domain antibodies with the CDR1, CDR2 and CDR3 as shown in combination in Table 1, including the framework regions. These single-domain antibodies and there CD1d binding properties as described in detail in the Examples disclosed herein. SEQ ID NO:1 corresponds with VHH nr 1; SEQ ID NO:2 corresponds with VHH nr 2; SEQ ID NO: 3 corresponds with VHH nr 3; SEQ ID NO:4 corresponds with VHH nr 4; SEQ ID NO:5 corresponds with VHH nr 5; SEQ ID NO: 6 corresponds with VHH nr 6; SEQ ID NO:7 corresponds with VHH nr 7; SEQ ID NO:8 corresponds with VHH nr 8; SEQ ID NO: 9 corresponds with VHH nr 9; SEQ ID NO:10 corresponds with VHH nr 10; SEQ ID NO:11 corresponds with VHH nr 11; SEQ ID NO: 12 corresponds with VHH nr 12; SEQ ID NO:13 corresponds with VHH nr 13; SEQ ID NO:14 corresponds with VHH nr 14; SEQ ID NO: 15 corresponds with VHH nr 18; SEQ ID NO:16 corresponds with VHH nr 19; SEQ ID NO: 17 corresponds with VHH nr 20; SEQ ID NO:18 corresponds with VHH nr 21; SEQ ID NO:19 corresponds with VHH nr 22; SEQ ID NO: 20 corresponds with VHH nr 23; and SEQ ID NO:21 corresponds with VHH nr 24 as shown in Table 1.

Also provided are single-domain antibodies comprised in the compound according to the invention and that has at least 70%,80%, 85%, 90%, 92%, 95%, 96%, 97%, 98% or at least 99% amino acid sequence identity with a sequence selected from the group consisting of SEQ ID N: 1-21, over its entire length (and as applicable for all sequence disclosed herein).

Although the compound according to the invention may be any kind of compound comprising a single-domain antibody that binds CD1d, in a preferred embodiment the compound is a polypeptide to which a pharmaceutical active agent or a label or a marker is attached. For example, the polypeptide, comprising the CD1d binding single-domain antibody may be linked to a pharmaceutical active agent that preferably is delivered to a CD1d expressing cell. Another example includes a compound according to the invention that comprises a CD1d-binding single-domain antibody and an antigen. Such compounds may find use in, for example, dendritic cell-based vaccines. The active agent may be linked to the compound according to the invention, preferably the polypeptide according to the invention, allowing release of the agent on its site of delivery. Another example is wherein the compound according to the invention, for example, the polypeptide according to the invention comprises a label. The label may be in the form of, for example, a fluorescent or radioactive label, but is not limited thereto. Any kind of label that allows for detecting the presence of or the localization of the compound according to the invention can suitably be used within the context of the invention. In another embodiment, the compound is a polypeptide.

However, and in addition, in another preferred embodiment of the invention, there is provided for a compound according to any of the previous claims wherein the compound comprises further single domain antibodies, wherein the compound comprises a label, wherein a pharmaceutical active agent is linked to the compound, wherein the single-domain antibody is humanized, wherein the compound is a bispecific or multispecific compound (bi-specificity or multi-specificity can allow the cross-linking of two antigens), wherein the compound is a bivalent or multivalent compound (bivalency or multi-valency can allow antibodies to bind to multimeric antigen with great avidity), wherein the compound is fused to an antigen, a peptide or a nucleotide sequence, wherein the compound is a liposome, a virus, and/or wherein the compound is a nanoparticle.

Also provided is a compound as disclosed herein wherein the single domain antibody binds to human CD1d but not to human CD1a, human CD1b and/or human CD1c. In other words, within the particular use intended, the compound according to the invention comprises a single domain antibody which specifically binds to human CD1d and not human CD1a, CD1b and/or CD1c. Preferable the compound according to the invention does bind to human CD1d and not to human CD1a, CD1b and/or CD1c. The single domain antibodies represented by SEQ ID NO 1-21 are examples of single domain antibodies that specifically bind with human CD1d. The skilled person knows how to determine without undue burden whether a single domain antibody is specific for human CD1d, as can be witnessed from the Examples.

As mentioned herein, it was surprisingly found that there can be provided for compounds comprising CD1d binding single domain antibodies that share high amino acid identity amongst them with respect to the CDR1, CDR2 and/or CDR3 sequences. In addition, it was found that there can be provided for compounds, comprising the single-domain antibodies as described herein, with different functional characteristics and features, as can be witnessed from the Examples. Therefore, there is also provided for a compound as taught herein, wherein the compound is capable of inducing maturation of dendritic cells, preferably of monocyte derived dendritic cells, preferably wherein the single-domain antibody has the complementarity determining regions CDR1, CDR2 and CDR3 as listed in combination for VHH2 or VHH5 in Table 1, or conservative sequence variants thereof, or wherein the single-domain antibody is VHH2 or VHH5 or conservative sequence variants thereof; and/or the compound is capable of inhibiting glycolipid, for example alpha-galactosyl ceramide, induced CD1d-restricted T-cell, such as invariant natural killer T-cell, activation, preferably wherein the single-domain antibody has the complementarity determining regions CDR1, CDR2 and CDR3 as listed in combination for VHH5 or VHH24 in Table 1, or conservative sequence variants thereof or wherein the single-domain antibody is VHH5 or VHH24 or conservative sequence variants thereof; and/or the compound is capable of inducing activation of CD1d-restricted T cells, such as invariant natural killer T-cells and/or stimulating glycolipid (e.g. alpha-galactosyl ceramide) induced activation of CD1d-restricted T cells, such as invariant natural killer T-cell, preferably wherein the single-domain antibody has the complementarity determining regions CDR1, CDR2 and CDR3 as listed in combination for VHH12 in Table 1, or conservative sequence variants thereof or wherein the single-domain antibody is VHH12 or conservative sequence variants thereof; and/or the compound is capable of inducing annexin V binding (for example, binding of annexin V to cells that were contacted with such compound; annexin V binding is a marker of early apoptosis) and/or apoptosis in CD1d-expressing cells, preferably CD1d-expressing tumor, preferably wherein the single-domain antibody has the complementarity determining regions CDR1, CDR2 and CDR3 as listed in combination for VHH3, VHH6, VHH8, or VHH19 in Table 1, or conservative sequence variants thereof, or wherein the single-domain antibody is VHH3 or VHH6 or VHH8 or VHH19 or conservative sequence variants thereof.

It was found that the single-domain antibodies VHH2 and VHH5, with the CDR's as shown in Table 1, show activity towards inducing maturation of dendritic cells, preferably of monocyte derived dendritic cells (see Examples), as well as cytokine production, exemplified by IL-12. Compounds comprising such single domain antibodies are useful in inducing dendritic cell maturation and cytokine production, e.g. IL-12 production, in vitro or in vivo, for example in the treatment of cancers, malaria and HIV and/or as an antimicrobial or anti-viral agent. In addition, CD1d-triggering on dendritic cells can be useful in vaccination approaches, as discussed herein (see, for example, Yue et al. (2010) J Immunol. 184(1):268-76; Yue et al. (2005) Proc Natl Acad Sci USA. 102(33):11811-6; Teng et al. (2009) J Immunol. 182(6):3366-71; or Teng et al. (2009) J Immunol. 183(3):1911-20)

In addition, it was found (see Examples) that there can be provided for a compound according to the invention that is capable of inhibiting glycolipid, i.e. all glycolipids that can be bound/presented by CD1d, for example, alpha-galactosyl ceramide, induced CD1d-restricted T-cell, such as invariant natural killer T-cell, activation, preferably wherein the single-domain antibody has the complementarity determining regions CDR1, CDR2 and CDR3 as listed for VHH5 or VHH24 in combination in Table 1, or conservative sequence variants thereof. Compounds comprising such single domain antibodies are useful in inhibiting glycolipid (e.g. alpha-galactosyl ceramide) induced CD1d-restricted T cell (including invariant natural killer T-cell) activation both in vitro or in vivo, for example in research and/or for rescueing iNKT (invariant Natural Killer T-cells) cells or other CD1d restricted T cell subsets from chronic overstimulation (see, for example, Terabe et al. (2014) Cancer Immunol Immunother. 63(3):199-213).

Furthermore there is provided for a compound according to the invention that is capable of inducing activation of CD1d-restricted T cells, including invariant natural killer T-cells and/or stimulating glycolipid (e.g. alpha-galactosyl ceramide) induced activation of CD1d-restricted T cells, including invariant natural killer T-cells, preferably wherein the single-domain antibody has the complementarity determining regions CDR1, CDR2 and CDR3 as listed in combination for VHH12 in Table 1, or conservative sequence variants thereof. Compounds comprising such single domain antibodies are useful in inducing invariant natural killer T-cell activation in the absence of exogenously added glycolipids and/or stimulating glycolipid (including alpha-galactosyl ceramide) induced invariant natural killer T-cell activation both in vitro or in vivo, for example in the treatment of cancer. iNKT cells can exert tumor cytotoxicity via (1) direct lysis of tumor cells or via (2) production of immunoregulatory cytokines (e.g. after interacting with DC) such as IFN-y that trigger secondary immune effectors such as NK cells, cytotoxic T cells to exert the antitumor effect. This is reviewed e.g. in Schneiders et al. (2011) Clin Immunol. 140(2):130-41.

In addition there is provided for a compound according to the invention that can bind to a CD1d targeting construct allowing targeting and targeted activation of iNKT cells at a tumor site, preferably wherein the single-domain antibody has the complementarity determining regions CDR1, CDR2 and CDR3 as listed in combination for VHH12 in Table 1, or conservative sequence variants thereof, preferably wherein the single-domain antibody is VHH12. This is useful and builds upon an approach put forward by Stirnemann K et al. J Clin Invest. 2008 March; 118(3):994-1005.

Also provided is a compound that is capable of inducing an increase in annexin V binding, which is suggestive of early apoptosis, and/or inducing apoptosis in CD1d-expressing cells, preferably CD1d-expressing tumor, preferably wherein the single-domain antibody has the complementarity determining regions CDR1, CDR2 and CDR3 as listed in combination for VHH3, VHH6, VHH8, or VHH19 in Table 1, or conservative sequence variants thereof. Compounds comprising such single domain antibodies are useful in inducing an increase in annexin V binding and/or apoptosis in CD1d-expressing cells both in vitro or in vivo, for example in the treatment of cancer. This is of use in, for example, CD1d+ malignancies where it can lead to cell death, for example in multiple myeloma (Blood. 2009 Mar. 12; 113(11):2498-507).

Also provided is for the use of such compounds comprising single domain antibodies with the different functionalities as described above, for example in the treatment of a condition in which such functionality is beneficial.

In a further preferred embodiment there is provided for a compound as described herein wherein the compound is a single domain antibody, preferably wherein the compound is a single domain antibody that has complementarity determining regions CDR1, CDR2 and CDR3 as listed in combination in Table 1, or conservative sequence variants thereof, or wherein the single domain antibody has an amino acid sequence selected from the group consisting of SEQ ID NO: 1-SEQ ID NO: 21, or conservative sequence variants thereof.

Also provided is a compound comprising an antibody, preferably a single-domain antibody which binds to human CD1d, wherein the antibody, preferably single-domain antibody comprises complementarity determining regions CDR1, CDR2 and CDR3 wherein CDR1, CDR2 and CDR 3 has an amino acid sequence that has at least 80%, 90%, 95% or 100% amino acid sequence identity to the amino acid sequence of respectively CDR1, CDR2 and CDR3 as shows for VHH nr 1, 2, 3, 4, 5, 6, 7, 8, 9, 10, 11, 12, 13, 14, 18, 19, 20, 21, 22, 23 or 24 as shown in Table 1. Preferably the compound, comprising an antibody, preferably a single-domain antibody has an amino acid sequence that has at least 80%, 90%, 95% or 100% amino acid sequence identity to the amino acid sequence of VHH nr 1, 2, 3, 4, 5, 6, 7, 8, 9, 10, 11, 12, 13, 14, 18, 19, 20, 21, 22, 23 or 24 as shown in Table 1, or conservative sequence variants thereof. Preferably to compound is an antibody, preferably a single stranded antibody. Each of the specific antibodies shown in table 1, or antibodies comprises the CDR1, CDR2, CDR3 as shown in combination therein (i.e. per VHH number) have surprising and non-obvious properties as shown in the examples and description. Also provided is a nucleic acid, or vector comprising such nucleic acid encoding for a CDR1, CDR2, and/or CDR3, antibody, single-domain antibody or compound according to the invention, as disclosed herein.

As will be appreciated by the skilled person, the compounds as described herein may have a wide variety of uses, including as a research tool, as a diagnostic tool, as means for delivery to a target site (expressing CD1d) of, for example, a drug, both in vitro and in vivo, in targeting two or more different receptors, molecules and/or antigens (e.g. wherein the compound is bi-specific or multi-specific), both in vitro and in vivo, and so on. Preferably the compound as described herein is for use in medical treatment, or for in vivo use as a diagnostic agent. Conditions that may benefit from the compound disclosed herein include, but are not limited to, cancer, HIV, malaria, asthma, allergy, autoimmune diseases, inflammatory bowel diseases and graft-versus-host-disease (GVHD). Therefore, in another embodiment, there is provided for a pharmaceutical composition comprising a compound according to the invention, for example comprising a single-domain antibody as described herein. As will be understood by the skilled person, the pharmaceutical composition may comprise another compound in addition to the compounds as disclosed herein, for example other pharmaceutical active ingredients and/or excipients.

Also provided is for the use of a compound as described herein, wherein the compound is used in vitro or wherein the compound is used in an in vitro diagnostic method, for example to detect CD1d expression in samples obtained from a patient, and/or to detect cells expressing CD1d.

According to another aspect of the invention, there is provided for a nucleotide sequence that encodes a compound as described herein. In this embodiment, the compound according to the invention is a polypeptide, for example the compound is a single domain antibody, for example with a sequence selected from the group consisting of SEQ ID NO: 1-21, and conservative sequence variants thereof.

The sequences as disclosed herein relate to amino acid sequences. Hence, the skilled person is well capable of providing for a nucleotide sequence encoding an amino acid sequence, as it only requires using a codon table to convert amino acid sequence into nucleotide sequence.

Such nucleotide sequence may be used to operably link it to promoter sequences, polyA signals etc., to provide for a genetic construct with which the antibody may be expressed.

Such a genetic construct comprising the nucleotide sequence may be comprised in a host cell. Such host cell or non-human organism comprising a nucleotide sequence according to the invention is also provided for.

In a preferred embodiment there is provided for a nucleotide sequence as disclosed herein, and that encodes for a compound comprising an amino acid sequence selected from the group consisting of SEQ ID NO: 22-SEQ ID NO: 42, or conservative sequence variants thereof and/or an amino acid sequence selected from the group consisting of SEQ ID NO: 43-SEQ ID NO: 63, or conservative sequence variants thereof and/or an amino acid sequence selected from the group consisting of SEQ ID NO: 64-SEQ ID NO: 84, or conservative sequence variants thereof.

Also provided is for a method for preparing a compound as disclosed herein, wherein the method comprises allowing a host cell comprising a nucleic acid according to the invention to express the compound; and obtaining the compound. Methods for expression and obtaining are readily known to the skilled person.

Finally, also provided is an antibody that comprises a CDR1 and/or CDR2 and/or CDR3, preferably a CDR1 and CDR2, even more preferably a CDR1, CDR2 and CDR3, wherein the CDR1 has an amino acid sequence selected from the group consisting of SEQ ID NO: 22-SEQ ID NO: 42, or conservative sequence variants thereof, the CDR2 has an amino acid sequence selected from the group consisting of SEQ ID NO: 43-SEQ ID NO: 63, or conservative sequence variants thereof and CDR3 has an amino acid sequence selected from the group consisting of SEQ ID NO: 64-SEQ ID NO: 84, or conservative sequence variants thereof. Preferably the complementarity determining regions CDR1, CDR2 and CDR 3 have an amino acid sequence that has at least 80%, 90%, 95% or 100% amino acid sequence identity to the amino acid sequence of respectively CDR1, CDR2 and CDR3 as shows for VHH nr 1, 2, 3, 4, 5, 6, 7, 8, 9, 10, 11, 12, 13, 14, 18, 19, 20, 21, 22, 23 or 24 as shown in Table 1.

The antibody may be any type of antibody, including a single domain antibody, a single chain antibody, a humanized antibody, a 4-chain antibody or any other immunoglobulin molecule. The antibody may be linked to other function or non-functional groups, for example the antibody may be a bi-specific or multi-specific antibody, and/or a bi-valent or multi-valent antibody, may comprise a label of be fused to e.g. a nanoparticle, a drug, a peptide, a nucleic acid, and so on, and as disclosed herein above. The antibody may be used in treatment of a (human) patient for example, in the treatment of cancer, or may be used to bind and detect human CD1d and/or cells expressing human CD1d.

Where the provided SEQ ID NO 22-84 in the sequence listing differs from the sequences shown in Table 1, the sequence shown in Table 1 prevails.

TABLE 1

VHH number, VHH reference number as used herein, and sequence of CDR1, CDR2 and CDR3 of the various CD1d antibodies of the invention.

| VHH nr (SEQ ID) | VHH ref | CDR1 (SEQ ID 22-42) | CDR2 (SEQ ID 43-63) | CDR3 (SEQ ID 64-84) |
|---|---|---|---|---|
| 1 (1) | 17-1E | GSSFSSYTMG | AIRWSGESPYYADSVKG | RLVPPGIPIERSLENMNYW |
| 2 (2) | 17-2B | GRSFSSYTMG | VIRWSGESPYYADSVKG | RLVPPGIPIERTLESMNYW |
| 3 (3) | 17-3D | GSSFSSYTMG | AIRWSGESPIYADSVKG | RLVPPGIPIERTLESMRYW |

TABLE 1-continued

VHH number, VHH reference number as used herein, and sequence of
CDR1, CDR2 and CDR3 of the various CD1d antibodies of the invention.

| VHH nr (SEQ ID) | VHH ref | CDR1 (SEQ ID 22-42) | CDR2 (SEQ ID 43-63) | CDR3 (SEQ ID 64-84) |
|---|---|---|---|---|
| 4 (4) | 17-4C | GRSFSSYTMG | AIRWSGESPYYADSVKG | RLVPPGIPIERTLESMKDW |
| 5 (5) | 17-7C | GSSFSSYTMG | GIRWSDESPIYADSVKG | RLVPPGIPIPRTSESMRYW |
| 6 (6) | 17-8B | GSSFSSYTMA | AIRWSGESPIYADSVKG | RLVPPGIPIERTLESMRYW |
| 7 (7) | 17-9C | VSSFSSYTMG | GIRWDDENPYYADSVKG | RLVPPGIPFERTLENMRYW |
| 18 (8) | 17-10B | GSSFSSYTMG | AIRWDGESPIYAESVKG | RLVPPGIPIERTLESMRYW |
| 19 (9) | 17-11B | GRSFSSYTMG | VIRWSGESPYYADSVKG | RLVPPGIPIERTLESMNYW |
| 10 (10) | 19-12G | GSSFSSYTMG | AIRWSDESPIYAGSVKG | RLVPPGIPIERTLESMRYW |
| 11 (11) | 17-13E | GSSFSSYTMG | AIRWSDESPYYSDSVKG | RLVPPGIPIERTLENMRYS |
| 12 (12) | 18-14B | GSMFSDNVMG | TIRTGGSTNYADSVKG | TIPVPSTPYDYW |
| 13 (13) | 19-15G | GRSFSSYTMG | AIRWSGESPYYADSVKG | RLVPPGIPIERTLENMNYW |
| 14 (14) | 19-22H | GSSFSSYTMG | AIRWSGESPYYADSVKG | RLVPPGIPIERTLESMNYW |
| 18 (15) | 19-21F | GSSFSSYTMG | AIRWSGESPIYADSVKG | RLVPPGIPIERTLESMKDW |
| 19 (16) | 19-23G | GSSFSSYTMT | GIRWSGESPYYADSVKG | RLVPPGIPIERTLESMRYW |
| 20 (17) | 19-24D | GSSFSSYTMG | AIRWSGESPYYGDSVKG | RLVPPGIPIGRTLESMNNW |
| 21 (18) | 19-25F | GSSFSSYTMG | AIRWSGESPYYADSVKG | RLVPPGIPIERALENMNYW |
| 22 (19) | 19-26A | GSSFSSYTMG | AIRWSDESPIYADSVKG | RLVPPGIPIERTLESMRYW |
| 23 (20) | 19-27F | GRSFSSYTMG | AIRWSGESPYYADSVKG | RLVPPGIPIERSLENMNYW |
| 24 (21) | 18-29C | GSIFSINAMG | VISSSGSTNYADSVKG | HVAGFDEYNYW |

TABLE 2

Sequence identity in CDR1, CDR2 and CDR3 compared to 17-1E

| | CDR1 | CDR2 | CDR3 |
|---|---|---|---|
| 17-2B | 90% | 94% | 89% |
| 17-3D | 100% | 94% | 84% |
| 17-4C | 90% | 100% | 79% |
| 17-7C | 100% | 82% | 73% |
| 17-8B | 90% | 94% | 84% |
| 17-9C | 90% | 76% | 84% |
| 17-10B | 100% | 82% | 84% |
| 17-11B | 90% | 94% | 89% |
| 19-12G | 100% | 82% | 84% |
| 17-13E | 100% | 88% | 84% |
| 18-14B | 60% | 64% | 21% |
| 19-15G | 90% | 100% | 95% |
| 19-22H | 100% | 100% | 89% |
| 19-21F | 100% | 94% | 79% |
| 19-23G | 90% | 94% | 84% |
| 19-24D | 100% | 94% | 79% |
| 19-25F | 100% | 100% | 95% |
| 19-26A | 100% | 88% | 84% |
| 19-27F | 90% | 100% | 100% |
| 18-29C | 60% | 64% | 15.7% |

EXAMPLES

Immunization

Two individual llamas (*Lama glama*) were immunized as described (Roovers R C et al. Cancer Immunol Immunother. 2007; 56:303-17). Briefly, $10^8$ stable CD1d transduced C1R-cells were injected s.c. on days 0, 14, 28 and 35. For phage display library construction 150 ml blood was collected on day 43.

Selection of CD1d Specific VHH

For construction of a phage display library peripheral blood lymphocytes (PBL) were isolated from the collected 150 ml blood samples. From the isolated lymphocytes, cDNA was prepared and used as template to amplify genes coding for the variable domains of the heavy-chain only antibodies. The PCR fragments were ligated into pUR8100 phagemid vector and transformed in *E. coli* cells. In this way, two VHH libraries were obtained which were subsequently expressed on phages and used for selection. For this purpose, phages from both libraries were incubated for 2 hours at 4° C. with CD1d transfected HeLa-cells. Cells were then washed and bound phages were eluted with 100 mM HCl for 7 minutes at 4° C. Removed phages were then neutralized with Tris-HCl followed by infection into *E. coli*. Selected phages were then counterselected twice for 1 hour at 4° C. using wild type C1R-cells, after which unbound phages were incubated for 1 hour with CD1d transfected C1R-cells. Bound phages were then eluted and infected to *E. coli* as described above. Bacteria were plated on agar plates containing 2% glucose/ampicillin to generate single bacterial colonies coding VHH DNA. VHH DNA from individual clones was digested with Sfi1/BstEII digestion enzymes and cloned into plasmid pMEK219, a derivative from pHen1 (Hoogenboom H R, et al. Nucleic Acids Res 1991; 19:4133-4137). With addition of a HC-V cassette to enable Sfi1/

BstEII cloning, and a C-terminal myc- and 6× HIS-tag deletion of the genIII sequence. pMEK219-VHH was transformed to E. coli TG1 bacteria.

An overnight culture was used to inoculate 2×TY medium plus 0.1% glucose and 100 ug/ml ampicillin. When OD600 reached IPTG was added to a final concentration of 1 mM. Protein production was allowed for 2-5 hours. Growth of all cultures was performed at 37° C. while vigorously shaking at 200-220 rpm. Protein production was stopped by spinning cultures for 15 minutes at 4° C. The bacterial pellet was resuspended in PBS and frozen for at least 1 hour at −80° C. Bacterial suspension was thawed, slightly shaken for 1 hour at 4° C. and spun at 4500 rpm for 30 minutes. Supernatant was used to confirm binding to CD1d transfected C1R-cells using flowcytometry.

CD1d Specificity of Selected VHH

Confirmation of CD1d specific binding was assessed by flowcytometry using C1R and K562 cells expressing either CD1a, CD1b, CD1c, or CD1d. Staining was performed in a 96-well plate and all incubations were performed in FACS buffer for 30 minutes at 4° C. For initial screenings of binding to CD1d, cells were incubated with 25 µl supernatant containing anti-CD1d VHH. After washing, cells were incubated with anti-myc tag antibody clone 4A6 (Merck Millipore, MA, USA), final dilution 1:500, washed and incubated with goat-anti-mouse F(ab)2 APC (Beckman Coulter, Fullerton, CA, USA), final dilution 1:200. After a final washing step, VHH binding to cells was assessed by flowcytometry (FACSFortessa, BD Biosciences). VHH showing specific binding were selected. As a positive control the anti-CD1d 51.1 mAb (eBiosciences Inc, New Jersey, USA) was used, as negative control a nanobody specific for azo-dye RR6 was used. Binding of the selected anti-CD1d VHH to CD1d was confirmed after purification (see below) and sequencing of anti-CD1d VHH. For these experiments, anti-CD1d VHH and controls were tested at a concentration of 5 µg/ml. Representative data is shown in FIG. 1.

Fingerprint Analysis and Sequencing

To select structurally different CD1d-specific VHH, DNA from selected VHHs was amplified by colony PCR, digested with Hinfl and subsequently run on a 2% agarose gel. Based on the digestion pattern different families could be selected. Individual families were then sequenced (BaseClear B.V. Leiden, The Netherlands) to confirm unique clones.

VHH Production and Purification

Supernatants containing unique anti-CD1d VHH were produced as described. For purification, these supernatants were subsequently incubated with washed Talon resin (Clontech, Mountain View, CA, USA) for 1 hour at room temperature. Talon resin was washed 3 times with PBS and once with 15 mM imidazole/PBS pH 7 and eluted with 150 mM imidazole/PBS pH 7. The eluted fraction was dialyzed twice for 24 h against PBS. Concentration of purified VHH was determined by Nanodrop measurement (Thermo Fisher Scientific Inc., Wilmington, DE, USA) and purity was confirmed by coomassie stained protein gel.

Anti-CD1d Mediated moDC Maturation

Immature monocyte derived dendritic cells (moDC) were generated as described (Lameris R. et al, Methods Mol Biol, 2014; 1139: 155-65). moDC were cultured in complete medium (RPMI-1640 containing HEPES, 10% FCS, 0.05 mM beta-mercaptoethanol, (β-ME), 100 IU/mL of sodium penicillin, 100 µg/mL of streptomycin sulfate, and 2.0 mM of l-glutamine) in 48-well plates at a concentration of $6*10^4$ cells/well in the presence of 5 ng/ml rhIL-4, 500 U/ml rhGM-CSF, 1000 U/ml rhINF-γ, 25 µg/ml polymyxin B and 500 nM anti-CD1d VHH or negative control VHH. LPS (200 ng/ml) was used as a positive control. After 24 h supernatants were taken for analysis of IL-12 and Il-10 production (not shown) (using ELISA). After 72 h cells were harvested and analyzed for expression of moDC maturation markers (PE labelled anti-CD86 (not shown), APC labelled anti-CD83, BD Biosciences) using flowcytometry (FACS Fortessa, BD Biosciences). Representative data is shown in FIG. 2.

Inhibition of αGalCer-Induced iNKT Activation by Anti-CD1d VHH iNKT cells were generated as described (Lameris R. et al, Methods Mol Biol 2014; 1139: 155-65). $5*10^4$ CD1d-transfected HeLa cells were cultured overnight at 37° C. in a 96-well plate in DMEM, containing 10% FCS, 0.05 mM β-ME, 100 IU/mL of sodium penicillin, 100 µg/mL of streptomycin sulfate, 2.0 mM of l-glutamine and 400 ng/ml α-GalCer. HeLa-CD1d cells were then washed and incubated with 500 nM anti-CD1d VHH (or negative control VHH) for 2 hours at 37° C. after which $5*10^4$ resting (<25% CD25 expression) iNKT were added. After 24 h, supernatants were harvested for detection of IFN-γ and IL-4 (using ELISA) while iNKT cells were harvested, resuspended in FACS buffer and analyzed by flow-cytometry in order to detect the induction (or inhibition) of iNKT cell activation (assessed by expression of the activation marker CD25 on iNKT cells (FACS Fortessa, BD Biosciences). See FIG. 3 and FIG. 7 for representative results with at least VHH24.

Induction of iNKT Cell Activation by Anti-CD1d VHH iNKT cells were generated as described (Lameris R. et al, Methods Mol Biol 2014; 1139: 155-65). $5*10^4$ CD1d-transfected HeLa cells, CD1d-transfected C1R cells and CD1d-transfected MM.1s cells were cultured overnight at 37° C. in a 96-well plate in DMEM, containing 10% FCS, 0.05 mM β-ME, 100 IU/mL of sodium penicillin, 100 µg/mL of streptomycin sulfate, 2.0 mM of l-glutamine in the presence or absence of 100 ng/ml α-GalCer or vehicle control. CD1d-transfected cells, loaded with α-GalCer or vehicle control, were then washed and incubated with 500 nM anti-CD1d VHH (or negative control VHH) for 2 hours at 37° C. after which $5*10^4$ resting (<25% CD25 expression) iNKT cells were added. After 24 h, supernatants were harvested for detection of IFN-γ and IL-4 (using ELISA) while iNKT cells were harvested, resuspended in FACS buffer and analyzed by flow-cytometry in order to assess the induction of iNKT cell activation (assessed by expression of the activation marker CD25 on iNKT cells (FACS Fortessa, BD Biosciences). See FIG. 4 and FIG. 8 (concentration dependency) for representative results; showing data for VHH12.

Analysis of Annexin V Binding Induced by Anti-CD1d VHH

CD1d-C1R and CD1d-MM.1s (as well as untransfected C1R and MM.1s cell lines as negative controls) were cultured at 37° C. in a 48-well plate at $1*10^5$ cells per well and incubated with 500 nM anti-CD1d VHH, negative control VHH, or anti-CD1d 51.1 mAb (as positive control). After 24 h, cells were stained with annexin V and propidium iodide (PI) according to manufacturers protocol (VPS Diagnostics, Hoeven, the Netherlands) and analyzed by flow cytometry (FACS Fortessa, BD Biosciences). Experimental results are shown in FIG. 5.

Induction of iNKT Cell Activation by Platebound CD1d and Anti-CD1d VHH iNKT cells were generated as described (Lameris R. et al, Methods Mol Biol 2014; 1139: 155-65). α-GalCer (1 mM) or vehicle control (100% DMSO) were heated for 2 minutes at 80° C., sonicated for 5 minutes and subsequently diluted in sterile, warm (37° C.) 0.1% triton-X to a concentration of 100 µM. Next 6 µM of a bispecific construct consisting of an anti-EGFR VHH fused to β2m-human CD1d was added in a 1:1 ratio. Final concentrations of α-GalCer and β2m-CD1d-anti-EGFR construct were 50 µM and 3 µM respectively. Vehicle and α-GalCer where incubated overnight at room temperature while shaking. 96-well plates were coated with anti-flag mAb (Sigma, clone M2; 1:1000) and incubated overnight at 4° C. The next day anti-flag coated plates were washed trice with PBS and incubated with α-GalCer or vehicle loaded construct diluted in PBS (construct concentration 0.5 µM) for 2 hours, while shaking at room temperature. After washing with PBS, coated plates were incubated with 250 nM anti-CD1d VHH for 2 hours at 37° C. after which $1*10^5$ resting (<25% CD25 expression) iNKT cells were added. After 24 h iNKT cells were harvested, resuspended in FACS buffer and analyzed by flow-cytometry in order to assess the induction of iNKT cell activation (assessed by expression of the activation marker CD25 on iNKT cells (FACS Fortessa, BD Biosciences). Results are presented in FIG. 6.

VHH12

In addition to the data shown above, additional experiments were performed using VHH12. The results of the experiments are shown in FIG. 9, FIG. 10 and FIG. 11. FIG. 9 shows induction of iNKT cell degranulation (left) and cytotoxicity against CD1d+ tumor cells line (right). FIG. 10 shows induction of iNKT cell cytotoxicity against CD1d+ primary multiple myeloma cells. FIG. 11 shows induction of iNKT cell cytokine production by anti-CD1d VHH12. For detection of cytokine production HeLa-CD1d cells were pulsed with vehicle control, OCH (a sphingosine truncated derivative of alpha-galactosylceramide (alpha-GC); glycolipid reported to induce Th2-cytokine production in iNKT cells) or αGC, incubated with anti-CD1d VHH and controls and co-cultured with iNKT for 24 h after which supernatants were analyzed (by Cytometric Bead Assay; CBA). N=4; *p<0.05; ****p<0.0001. The anti-CD1d VHH shown is VHH12.

Results

Representative results of the various experiments is shown in the Figures and the accompanying legends; additional experimental data is discussed above in the context of the current invention.

---

The invention claimed is:

1. A compound comprising a single domain antibody that binds to CD1d, comprising a complementarity determining region (CDR)-1, CDR2, and CDR3, wherein;
   a. the CDR1 comprises an amino acid sequence of SEQ ID NO: 24, the CDR2 comprises an amino acid of SEQ ID NO: 45, and the CDR3 comprises an amino acid of SEQ ID NO: 66;
   b. the CDR1 comprises an amino acid sequence of SEQ ID NO: 26, the CDR2 comprises an amino acid of SEQ ID NO: 47, and the CDR3 comprises an amino acid of SEQ ID NO: 68;
   c. the CDR1 comprises an amino acid sequence of SEQ ID NO: 27, the CDR2 comprises an amino acid of SEQ ID NO: 48, and the CDR3 comprises an amino acid of SEQ ID NO: 69;
   d. the CDR1 comprises an amino acid sequence of SEQ ID NO: 29, the CDR2 comprises an amino acid of SEQ ID NO: 50, and the CDR3 comprises an amino acid of SEQ ID NO: 71; or
   e. the CDR1 comprises an amino acid sequence of SEQ ID NO: 37, the CDR2 comprises an amino acid of SEQ ID NO: 58, and the CDR3 comprises an amino acid of SEQ ID NO: 79.

2. The compound of claim 1, wherein the single domain antibody binds to human CD1d but not to human CD1a human CD1b and/or human CD1c.

3. A pharmaceutical composition comprising the compound of claim 1 and a pharmaceutically acceptable carrier.

4. A nucleotide sequence encoding the compound of claim 1.

5. An isolated host cell or non-human organism comprising a nucleotide sequence encoding the compound of claim 1.

6. The compound of claim 1, further comprising an additional single domain antibody.

7. The compound of claim 1, wherein the compound is a bispecific or multispecific compound.

8. The compound of claim 1, wherein the compound is linked to an antibody.

9. A compound comprising a single domain antibody that binds to CD1d, comprising a complementarity determining region (CDR)-1, CDR2, and CDR3, wherein the CDR1 comprises SEQ ID NO: 37, the CDR2 comprises SEQ ID NO: 58, and the CDR3 comprises SEQ ID NO: 79.

10. The compound of claim 9, further comprising an additional single domain antibody.

11. The compound of claim 9, wherein the compound is a bispecific or multispecific compound.

12. The compound of claim 9, wherein the compound is linked to an antibody.

13. A pharmaceutical composition comprising the compound of claim 9 and a pharmaceutically acceptable carrier.

14. A nucleotide sequence encoding the compound of claim 9.

15. An isolated host cell or non-human organism comprising a nucleotide sequence encoding the compound of claim 9.

* * * * *